US012557974B2

(12) United States Patent
Baba

(10) Patent No.: US 12,557,974 B2
(45) Date of Patent: Feb. 24, 2026

(54) OBJECTIVE LENS FOR AN ENDOSCOPE AND ENDOSCOPE

(71) Applicant: FUJIFILM CORPORATION, Tokyo (JP)

(72) Inventor: Tomoyuki Baba, Saitama (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 18/916,774

(22) Filed: Oct. 16, 2024

(65) Prior Publication Data

US 2025/0151988 A1     May 15, 2025

(30) Foreign Application Priority Data

Nov. 10, 2023     (JP) ................................. 2023-192435

(51) Int. Cl.
*A61B 1/00*          (2006.01)
*A61B 1/05*          (2006.01)

(52) U.S. Cl.
CPC .............. *A61B 1/0019* (2013.01); *A61B 1/05* (2013.01)

(58) Field of Classification Search
CPC ..... A61B 1/0019; A61B 1/05; A61B 1/00096; G02B 23/243
See application file for complete search history.

(56) References Cited

U.S. PATENT DOCUMENTS

| | | | | |
|---|---|---|---|---|
| 4,976,522 | A | 12/1990 | Igarashi | |
| 5,999,329 | A * | 12/1999 | Ohtake | G02B 15/177 |
| | | | | 359/686 |
| 6,353,504 | B1 | 3/2002 | Yamamoto | |
| 2002/0055669 | A1 | 5/2002 | Konno | |
| 2011/0075273 | A1 | 3/2011 | Mizusawa | |
| 2013/0286276 | A1* | 10/2013 | Kawamura | G02B 15/1461 |
| | | | | 348/345 |
| 2014/0267877 | A1* | 9/2014 | Nakagawa | G02B 15/145121 |
| | | | | 359/683 |
| 2016/0349505 | A1* | 12/2016 | Kawamura | G02B 5/005 |
| 2022/0050284 | A1 | 2/2022 | Yamamoto et al. | |
| 2025/0151988 | A1* | 5/2025 | Baba | G02B 23/243 |
| 2025/0306350 | A1* | 10/2025 | Kondo | G02B 15/16 |

FOREIGN PATENT DOCUMENTS

| | | | | | |
|---|---|---|---|---|---|
| CN | 102460266 | B | * | 10/2014 | ............. G02B 7/105 |
| JP | H01-279219 | A | | 11/1989 | |
| JP | 2000-330020 | A | | 11/2000 | |

(Continued)

*Primary Examiner* — Michael Lee

(74) *Attorney, Agent, or Firm* — SOLARIS Intellectual Property Group, PLLC

(57)          ABSTRACT

The objective lens for an endoscope consists of, from an object side to an image side, a first lens group having positive optical power and a second lens group having positive optical power. During focusing, only the second lens group moves. The first lens group includes a single lens that has negative optical power closest to the object side. The objective lens for an endoscope satisfies conditional expressions determined in advance related to a maximum image height, a focal length of a whole system, a maximum half angle of view, a focal length of the first lens group, a focal length of the second lens group, and a focal length of the single lens of the first lens group.

17 Claims, 12 Drawing Sheets

EXAMPLE 1

FARTHEST POINT
OBSERVATION STATE

NEAREST POINT
OBSERVATION STATE

(56)           References Cited

FOREIGN PATENT DOCUMENTS

| JP | 2001-091832 A | 4/2001 |
| JP | 2002-014282 A | 1/2002 |
| JP | 2002-028126 A | 1/2002 |
| JP | 2011-075915 A | 4/2011 |
| JP | 2016-001335 A | 1/2016 |
| JP | 2021-032954 A | 3/2021 |
| JP | 2022-033521 A | 3/2022 |
| WO | 2019/163744 A1 | 8/2019 |

* cited by examiner

EXAMPLE 1

EXAMPLE 1

FARTHEST POINT
OBSERVATION STATE

NEAREST POINT
OBSERVATION STATE

EXAMPLE 2

FARTHEST POINT
OBSERVATION STATE

NEAREST POINT
OBSERVATION STATE

EXAMPLE 2

EXAMPLE 3

FARTHEST POINT
OBSERVATION STATE

NEAREST POINT
OBSERVATION STATE

EXAMPLE 3

EXAMPLE 4

FARTHEST POINT
OBSERVATION STATE

NEAREST POINT
OBSERVATION STATE

EXAMPLE 4

EXAMPLE 5

FARTHEST POINT
OBSERVATION STATE

NEAREST POINT
OBSERVATION STATE

OBJECTIVE LENS FOR AN ENDOSCOPE AND ENDOSCOPE

CROSS-REFERENCE TO RELATED APPLICATIONS

This application claims priority from Japanese Patent Application No. 2023-192435, filed on Nov. 10, 2023, the entire disclosure of which is incorporated herein by reference.

BACKGROUND

Technical Field

The present disclosure relates to an objective lens for an endoscope and an endoscope.

Related Art

In the related art, devices described in JP2022-033521A, JP2011-075915A, JP2002-028126A, WO2019/163744A, and JP2001-091832A are known as objective lenses used in endoscopes.

SUMMARY

An objective lens for an endoscope that has a focusing function and that maintains a favorable optical performance in observation over an entire range of an object distance from a farthest point to a nearest point is required. This requirement level is increasing year by year.

The present disclosure has been devised in view of the circumstances, and an object thereof is to provide an objective lens for an endoscope that has a focusing function and that maintains a favorable optical performance in observation over an entire range of an object distance from a farthest point to a nearest point and an endoscope comprising the objective lens for an endoscope.

According to an aspect of the present disclosure, there is provided an objective lens for an endoscope consisting of, in order from an object side to an image side, a first lens group having positive optical power and a second lens group having positive optical power, in which during focusing from a farthest point object to a nearest point object, the first lens group is fixed to an image plane, and only the second lens group moves along an optical axis, the first lens group includes a single lens having negative optical power closest to the object side, and conditional expressions (1), (2), and (3) are satisfied, which are represented by $$0 < Y/(fF \times \tan \omega f) < 0.6 \tag{1},$$

$$0 < f1/f2 < 0.25 \tag{2, and}$$

$$-1.2 < fL1/fF < 0 \tag{3}.$$

Symbols in each conditional expression are defined as follows. A maximum image height is denoted by Y. A focal length of a whole system in a state where the farthest point object is in focus is denoted by fF. A maximum half angle of view in the state where the farthest point object is in focus is denoted by $\omega f$. A focal length of the first lens group is denoted by f1. A focal length of the second lens group is denoted by f2. A focal length of the single lens of the first lens group is denoted by fL1.

It is preferable that in a case where an F-number in the state where the farthest point object is in focus is denoted by FNof, in the objective lens for an endoscope of the aspect, conditional expression (4) is satisfied, which is represented by $$0 < FNof/\tan \omega f < 2 \tag{4}.$$

It is preferable that in the objective lens for an endoscope of the aspect, conditional expression (5) is satisfied, which is represented by $$0 < fF/f1 < 2 \tag{5}.$$

It is preferable that in the objective lens for an endoscope of the aspect, conditional expression (6) is satisfied, which is represented by $$0 < fF/f2 < 0.5 \tag{6}.$$

It is preferable that in the objective lens for an endoscope of the aspect, conditional expression (7) is satisfied, which is represented by $$-1.5 < fL1/f1 < \tag{7}.$$

It is preferable that a lens surface of the single lens of the first lens group on the object side is a plane.

It is preferable that in a configuration where the first lens group consists of, in order from the object side to the image side, a first a lens group having positive optical power, an aperture stop, and a first b lens group having positive optical power, in a case where a focal length of the first a lens group is denoted by f1a, in the objective lens for an endoscope of the aspect, conditional expression (8) is satisfied, which is represented by $$0 < fF/f1a < 1 \tag{8}.$$

It is preferable that in a configuration where the first lens group consists of, in order from the object side to the image side, a first a lens group having positive optical power, an aperture stop, and a first b lens group having positive optical power, in a case where a focal length of the first a lens group is denoted by f1a, in the objective lens for an endoscope of the aspect, conditional expression (9) is satisfied, which is represented by $$0 < f1/f1a < 1 \tag{9}.$$

It is preferable that in a configuration where the first lens group consists of, in order from the object side to the image side, a first a lens group having positive optical power, an aperture stop, and a first b lens group having positive optical power, in a case where a focal length of the first b lens group is denoted by f1b, in the objective lens for an endoscope of the aspect, conditional expression (10) is satisfied, which is represented by $$0 < fF/f1b < 1 \tag{10}.$$

It is preferable that in a configuration where the first lens group consists of, in order from the object side to the image side, a first a lens group having positive optical power, an aperture stop, and a first b lens group having positive optical power, in a case where a focal length of the first b lens group is denoted by f1b, in the objective lens for an endoscope of the aspect, conditional expression (11) is satisfied, which is represented by $$0 < f1/f1b < 1 \qquad (11).$$

It is preferable that in a case where, during focusing from the farthest point object to the nearest point object, a distance by which the second lens group moves is denoted by M, a paraxial imaging magnification of the whole system in the state where the farthest point object is in focus is denoted by $\beta f$, and a paraxial imaging magnification of the whole system in a state where the nearest point object is in focus is denoted by $\beta n$, in the objective lens for an endoscope of the aspect, expression (12) is satisfied, which is represented by $$0.01 < (|F/|M|) \times (\beta f / \beta n) < 1 \qquad (12).$$

It is preferable that in a configuration where the first lens group consists of, in order from the object side to the image side, a first a lens group having positive optical power, an aperture stop, and a first b lens group having positive optical power, the first a lens group includes a cemented lens in which at least one negative lens and at least one positive lens are cemented.

It is preferable that in a case where an average value of abbe numbers of all the positive lenses included in the cemented lens of the first a lens group based on a d line is denoted by $\nu1p$, and an average value of abbe numbers of all the negative lenses included in the cemented lens of the first a lens group based on the d line is denoted by $\nu1n$, in the objective lens for an endoscope of the aspect, conditional expression (13) is satisfied, which is represented by $$0 < |\nu1p - \nu1n| < 40 \qquad (13).$$

It is preferable that the second lens group includes a cemented lens in which at least one negative lens and at least one positive lens are cemented.

The second lens group may be configured to consist of one cemented lens in which at least one negative lens and at least one positive lens are cemented.

It is preferable that in a case where an average value of abbe numbers of all the positive lenses included in the cemented lens of the second lens group based on a d line is denoted by $\nu2p$, and an average value of abbe numbers of all the negative lenses included in the cemented lens of the second lens group based on the d line is denoted by $\nu2n$, in the objective lens for an endoscope of the aspect, conditional expression (14) is satisfied, which is represented by $$25 < |\nu2p - \nu2n| < 85 \qquad (14).$$

According to another aspect of the present disclosure, there is provided an endoscope comprising the objective lens for an endoscope according to the aspect of the present disclosure.

"Consisting of" and "consist of" in the present specification may intend to include a lens substantially not having optical power, optical elements other than a lens, such as a stop, a filter, and cover glass, a lens flange, a lens barrel, an imaging element, and the like, other than the described components.

The term "a group having positive optical power" in the present specification means that a group having positive optical power as a whole group. The terms "a lens having positive optical power" and "a positive lens" are synonymous. The terms "a lens having negative optical power" and "a negative lens" are synonymous. The term "-lens group"

is not limited to a configuration consisting of a plurality of lenses, but may be a configuration consisting of only one lens.

The term "a single lens" means one lens that is not cemented. However, a compound aspherical lens (a lens in which a lens (for example, a spherical lens) and an aspherical film formed on the spherical lens are integrally formed and which functions as one aspherical lens as a whole) is not regarded as a cemented lens, but regarded as one lens. The reference numeral of optical power and a surface shape of a lens including an aspherical surface will be used in terms of a paraxial region unless stated otherwise.

In the present specification, the "whole system" means the objective lens for an endoscope. The term "focal length" used in conditional expressions means a paraxial focal length. Values used in conditional expressions are values in a case where the d line is set as reference. The "d line", a "C line", an "F line", and an "h line" described in the present specification are emission lines, and a wavelength of the d line is 587.56 nanometers (nm), a wavelength of the C line is 656.27 nanometers (nm), a wavelength of the F line is 486.13 nanometers (nm), and a wavelength of the h line is 404.66 nanometers (nm).

With the present disclosure, the objective lens for an endoscope that has a focusing function and that maintains a favorable optical performance in observation over an entire range of an object distance from a farthest point to a nearest point and the endoscope comprising the objective lens for an endoscope can be provided.

DESCRIPTION OF EMBODIMENTS

Hereinafter, an embodiment of the present disclosure will be described with reference to the drawings.

With an endoscope, there are a requirement to observe a wide range as a whole and a requirement to partially observe an affected area or the like found in the overall observation in detail. In order to observe the wide range as a whole, the observation is performed in a state of being separated from an object, which is an observation target, using an observation optical system having a wide angle of view, and this state corresponds to a far-side observation state. On the other hand, in order to observe a part of the affected area or the like in detail, the object, which is the observation target, is observed in a state where the endoscope is brought closer to the object, and this state corresponds to a near-side observation state. In order to satisfy the two requirements described above, it is required that an objective lens for an endoscope has a focusing function such that an entire range of an object distance from a farthest point to a nearest point can be favorably observed. Hereinafter, in the objective lens for an endoscope, a state where a farthest point object is in focus will be referred to as a farthest point observation state, and a state where a nearest point object is in focus will be referred to as a nearest point observation state.

Figure 1:
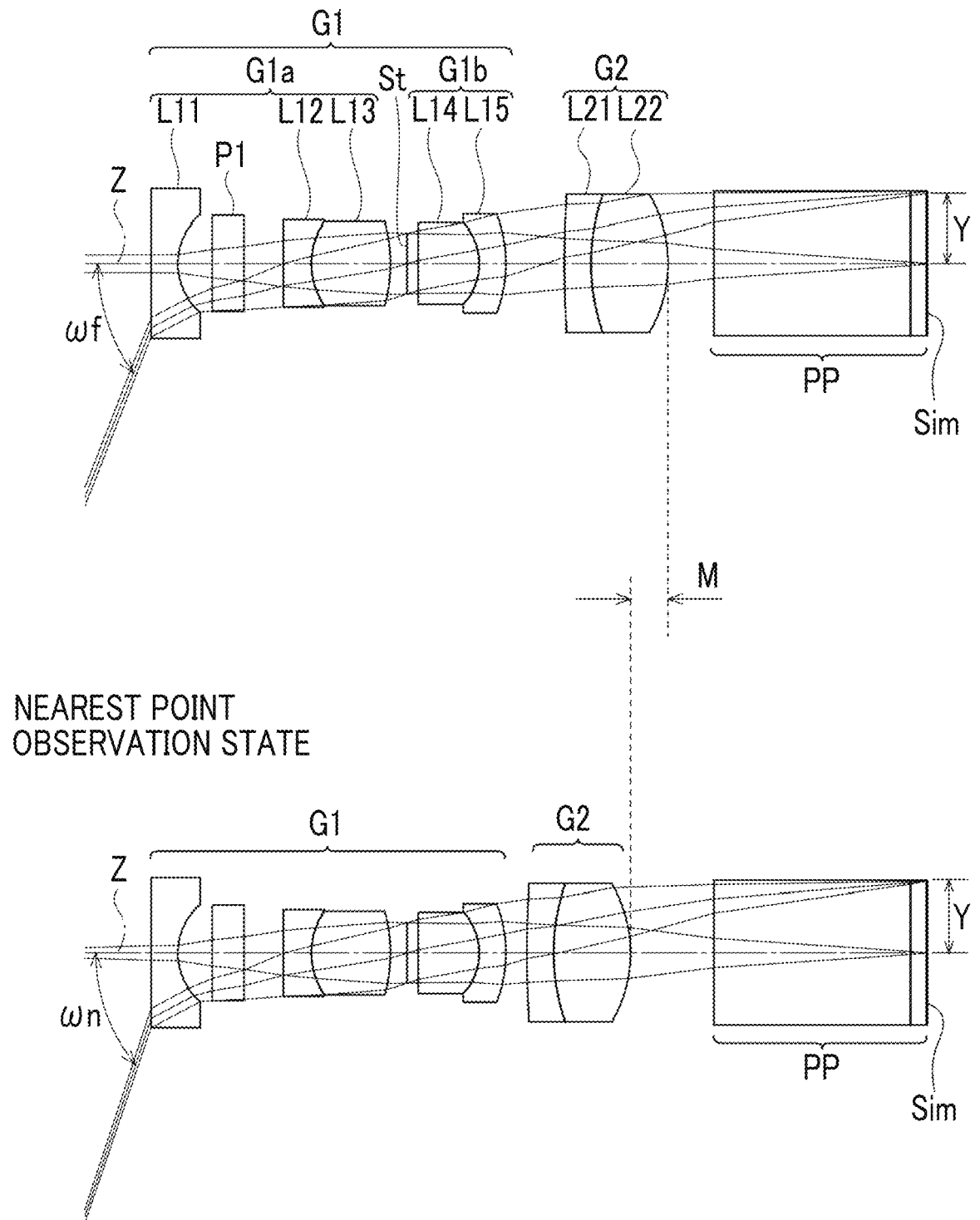
FIG. 1 is a cross-sectional view showing a configuration and luminous flux of an objective lens for an endoscope according to an embodiment corresponding to an objective lens for an endoscope of example 1.

FIG. 1 shows a configuration and luminous flux in a cross section including an optical axis Z of the objective lens for an endoscope according to the embodiment of the present disclosure. An example shown in FIG. 1 corresponds to example 1 to be described later. In FIG. 1, a left side is an object side and a right side is an image side. In FIG. 1, the farthest point observation state is shown in an upper part and the nearest point observation state is shown in a lower part. In FIG. 1, the luminous flux is on-axis luminous flux and luminous flux of a maximum half angle of view of in the farthest point observation state and on-axis luminous flux and luminous flux of a maximum half angle of view on in the nearest point observation state.

The objective lens for an endoscope according to the embodiment of the present disclosure consists of a first lens group G1 that has positive optical power and a second lens group G2 that has positive optical power, in order from the object side to the image side along the optical axis Z. With such a configuration, there is an advantage in securing a favorable optical performance in observation over the entire range of an object distance from a farthest point to a nearest point.

For example, each group in the example in FIG. 1 is composed as follows. The first lens group G1 consists of a lens L11, an optical member P1, a lens L12, a lens L13, an aperture stop St, a lens L14, and a lens L15, in order from the object side to the image side. The second lens group G2 consists of a lens L21 and a lens L22, in order from the object side to the image side. The optical member P1 is assumed to be a filter or the like and is a member that has an incident surface and an emission surface which are parallel to each other and that does not have optical power. The aperture stop St in FIG. 1 does not indicate a size or a shape, but indicates a position on the optical axis.

In the example of FIG. 1, an optical member PP in which an incident surface and an emission surface are parallel to each other is disposed between the lens L22 and an image plane Sim. The optical member PP is a member assuming a prism, a filter, cover glass, and the like. The optical member PP is a member that does not have optical power, and a configuration where the optical member PP is omitted is also possible.

The objective lens for an endoscope according to the embodiment of the present disclosure has a focusing function. During focusing from the farthest point object to the nearest point object, the first lens group G1 is fixed to the image plane Sim, and only the second lens group G2 moves along the optical axis Z. That is, the present disclosure adopts a rear focus type configuration where only one lens group moves during focusing. According to the configuration of the present disclosure, a structure required for focusing can be simplified compared to a type in which a plurality of lens groups move during focusing and an inner focus type. In addition, as in the present disclosure, there is an advantage in securing airtightness as the first lens group G1, which is a lens group closest to the object side, is stationary during focusing. In the endoscope, the objective lens for an endoscope is often mounted on the endoscope without a protective member, and a lens closest to the object side, in the objective lens for an endoscope, is often made to have a function of an optical window. Since airtightness is required to be maintained in that case, there is an advantage in the first lens group G1 having a stationary configuration.

Figure 2:
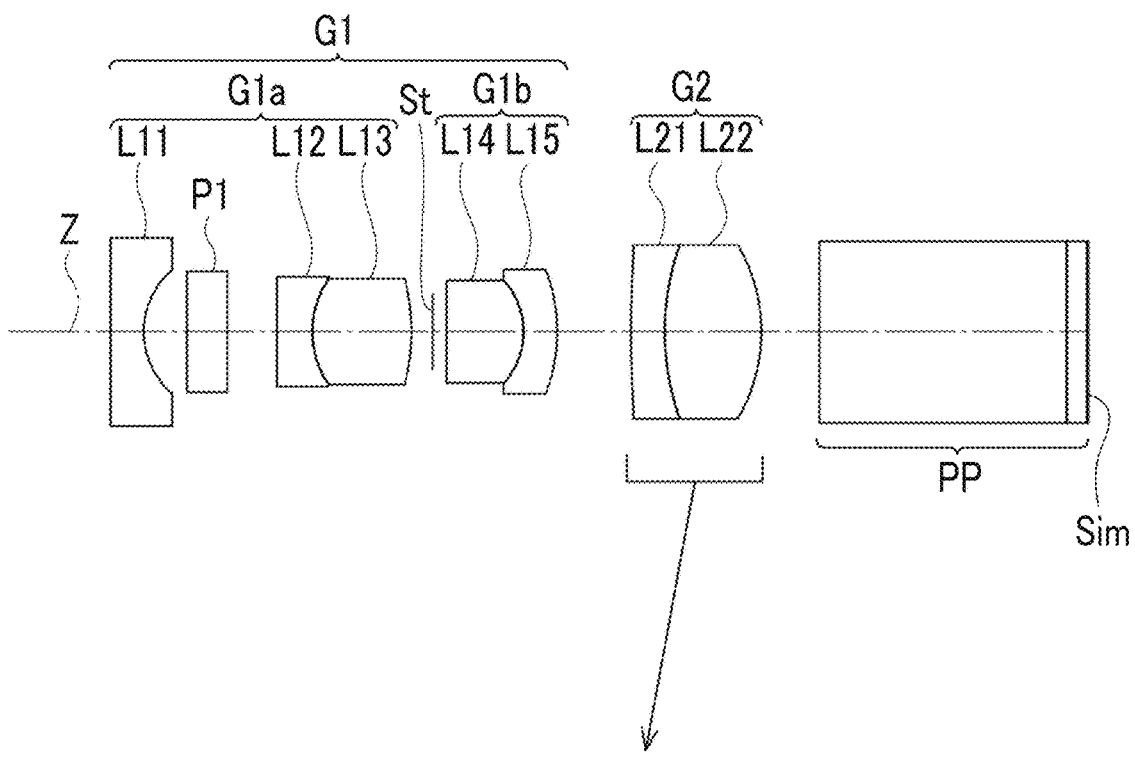
FIG. 2 is a cross-sectional view showing the configuration of the objective lens for an endoscope of example 1.
Figure 2:
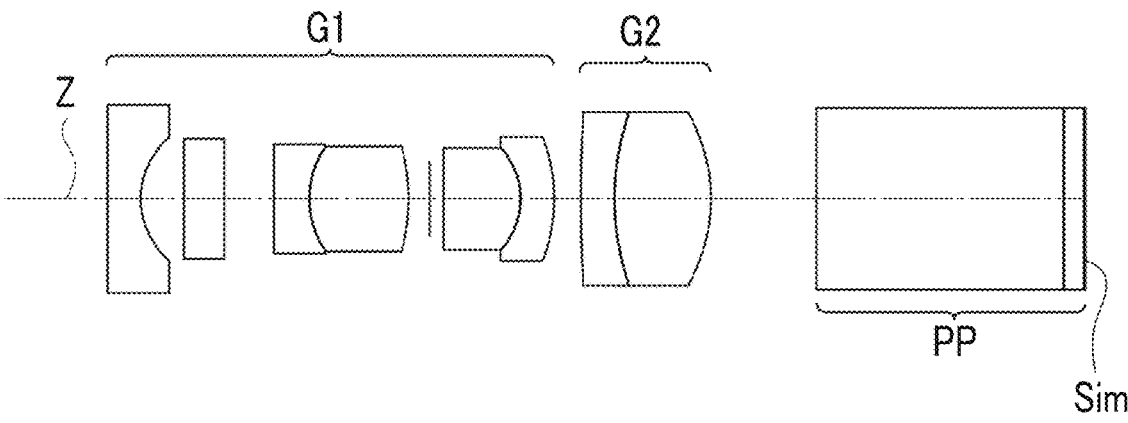

For example, in the example of FIG. 1, the second lens group G2 moves to the object side during focusing from the farthest point object to the nearest point object. FIG. 2 is a cross-sectional view showing a configuration of the objective lens for an endoscope of FIG. 1. A basic showing method of FIG. 2 is the same as that of FIG. 1. However, in FIG. 2, showing of luminous flux is omitted, and an arrow indicating a schematic movement direction of the second lens group G2 during focusing from the farthest point object to the nearest point object is written between the upper part and the lower part.

The first lens group G1 includes a single lens that is closest to the object side and that has negative optical power. With this configuration, there is an advantage in achieving both of an increase in angle of view and a reduction in size of a lens system.

It is preferable that a lens surface of a single lens on the object side, which is closest to the object side of the first lens group G1 and which has negative optical power, is a plane. In such a case, there is an advantage in suppressing an increase in an outer diameter of the single lens which is closest to the object side and which has negative optical power. In addition, the manufacturability of the single lens can be improved, and the adhesion of a liquid or the like to a surface of the single lens on the object side can be reduced.

It is preferable that the first lens group G1 consists of a first a lens group G1a that has positive optical power, the aperture stop St, and a first b lens group G1b that has positive optical power, in order from the object side to the image side. In such a case, there is an advantage in securing a favorable optical performance in observation over the entire range of an object distance from a farthest point to a nearest point.

For example, in the example of FIG. 1, the first a lens group G1a consists of the lens L11, the optical member P1, the lens L12, and the lens L13 in order from the object side to the image side, and the first b lens group G1b consists of the lens L14 and the lens L15 in order from the object side to the image side.

It is preferable that the first a lens group G1a includes a cemented lens in which at least one negative lens and at least one positive lens are cemented. In such a case, there is an advantage in suppressing longitudinal chromatic aberration and lateral chromatic aberration from a visible range to a short wavelength range near a wavelength of 400 nm.

It is preferable that the second lens group G2 includes a cemented lens in which at least one negative lens and at least one positive lens are cemented. In such a case, there is an advantage in suppressing longitudinal chromatic aberration and lateral chromatic aberration from a visible range to a short wavelength range near a wavelength of 400 nm.

The second lens group G2 may be configured to consist of one cemented lens in which at least one negative lens and at least one positive lens are cemented. In such a case, there is an advantage in suppressing axial chromatic aberration and lateral chromatic aberration from a visible range to a short wavelength range near a wavelength of 400 nm while suppressing an increase in size of the lens system. The second lens group G2 may be configured to consist of one cemented lens in which one negative lens and one positive lens are cemented. In such a case, in addition to the effects described above, there is an advantage in achieving a reduction in size of the lens system.

Next, a preferable configuration and a possible configuration related to a conditional expression of the objective lens for an endoscope according to the embodiment of the present disclosure will be described. In the description related to the following conditional expression, redundant description of symbols will be omitted by using the same symbol for the same definition in order to avoid lengthy description. In addition, hereinafter, the "objective lens for an endoscope according to the embodiment of the present disclosure" will also be simply referred to as the "objective lens for an endoscope" in order to avoid lengthy description.

It is preferable that the objective lens for an endoscope satisfies the following conditional expression (1). Herein, a maximum image height is Y. A focal length of the whole system in a state where a farthest point object is in focus is fF. A maximum half angle of view in the state where the farthest point object is in focus is denoted by $\omega$f. Tan is a tangent. For example, FIG. 1 shows the maximum image height Y and the maximum half angle of view of described above. Since Y>0, fF>0, and tan $\omega$f>0, a lower limit of conditional expression (1) is 0<Y/(fF×tan $\omega$f). By not allowing a corresponding value of conditional expression (1) to be equal to or greater than an upper limit value, there is an advantage in increasing a magnification near the center of an image forming region while performing observation with a wide visual field.

$$0<Y/(fF\times\tan \omega f)<0.6 \tag{1}$$

In addition, it is preferable that the objective lens for an endoscope satisfies the following conditional expression (1-1). By not allowing a corresponding value of conditional expression (1-1) to be equal to or less than a lower limit value, an increase in an outer diameter of the lens can be suppressed.

$$0.2<Y/(fF\times \tan \omega f)<0.6 \tag{1-1}$$

In order to obtain more favorable characteristics, it is more preferable to set upper limit values of conditional expression (1) and conditional expression (1-1) to 0.4. For example, it is more preferable that the objective lens for an endoscope satisfies the following conditional expression (1-2).

$$0.2<Y/(fF\times\tan \omega f)<0.4 \tag{1-2}$$

In a case where a focal length of the first lens group G1 is denoted by f1 and a focal length of the second lens group G2 is denoted by f2, it is preferable that the objective lens for an endoscope satisfies the following conditional expression (2). Since both the first lens group G1 and the second lens group G2 are lens groups that have positive optical power, f1>0 and f2>0 are satisfied. Thus, a lower limit of conditional expression (2) is 0<f1/f2. Since it is easy to maintain a good balance between respective types of aberration by satisfying conditional expression (2), there is an advantage in securing a favorable optical performance in observation over an entire range of an object distance from a farthest point to a nearest point.

$$0<f1/f2<0.25 \tag{2}$$

In order to obtain more favorable characteristics, it is preferable that the objective lens for an endoscope satisfies the following conditional expression (2-1).

$$0<f1/f2<0.22 \tag{2-1}$$

In a case where a focal length of a single lens, which is closest to the object side and which has negative optical power, in the first lens group G1 is denoted by fL1, it is preferable that the objective lens for an endoscope satisfies the following conditional expression (3). By not allowing a corresponding value of conditional expression (3) to be equal to or less than a lower limit value, there is an advantage in achieving both an increase in angle of view and a reduction in size of the lens system. An upper limit of conditional expression (3) is fL1/fF<0 since fL1<0 and fF>0 are satisfied.

$$-1.2<fL1/fF<0 \tag{3}$$

In addition, it is preferable that the objective lens for an endoscope satisfies the following conditional expression (3-1). By not allowing a corresponding value of conditional expression (3-1) to be equal to or greater than an upper limit value, it is advantageous in securing a favorable optical performance in observation over the entire range of an object distance from a farthest point to a nearest point.

$$-1.2<fL1/fF<-0.8 \tag{3-1}$$

In order to obtain more favorable characteristics, it is more preferable to set lower limit values of conditional expression (3) and conditional expression (3-1) to −1.1. For example, it is more preferable that the objective lens for an endoscope satisfies the following conditional expression (3-2).

$$-1.1<fL1/fF<-0.8 \tag{3-2}$$

In a case where an F-number in a state where a farthest point object is in focus is denoted by FNo, it is preferable that the objective lens for an endoscope satisfies the following conditional expression (4). Since FNof>0 and tan $\omega$f>0 are satisfied, a lower limit of conditional expression (4) is 0<FNof/tan $\omega$f. By not allowing a corresponding value of conditional expression (4) to be equal to or greater than an upper limit value, there is an advantage in increasing an angle of view of the lens system while securing a small F-number.

$$0<FNof/\tan \omega f<2 \tag{4}$$

In addition, it is preferable that the objective lens for an endoscope satisfies the following conditional expression (4-1). By not allowing a corresponding value of conditional expression (4-1) to be equal to or less than a lower limit value, there is an advantage in securing a favorable optical performance in observation over the entire range of an object distance from a farthest point to a nearest point.

$$0.6<FNof/\tan \omega f<2 \tag{4-1}$$

In order to obtain more favorable characteristics, it is more preferable to set upper limit values of conditional expression (4) and conditional expression (4-1) to 1.6. For example, it is more preferable that the objective lens for an endoscope satisfies the following conditional expression (4-2).

$$0.6<FNof/\tan \omega f<1.6 \tag{4-2}$$

It is preferable that the objective lens for an endoscope satisfies the following conditional expression (5). Since fF>0 and f1>0 are satisfied, a lower limit of conditional expression (5) is 0<fF/f1. By not allowing a corresponding value of conditional expression (5) to be equal to or greater than an upper limit value, it is advantageous in securing a favorable optical performance in observation over the entire range of an object distance from a farthest point to a nearest point.

$$0<fF/f1<2 \qquad (5)$$

In addition, it is preferable that the objective lens for an endoscope satisfies the following conditional expression (5-1). By not allowing a corresponding value of conditional expression (5-1) to be equal to or less than a lower limit value, there is an advantage in suppressing an increase in size of the lens system.

$$0.5<fF/f1<2 \qquad (5-1)$$

In order to obtain more favorable characteristics, it is more preferable to set upper limit values of conditional expression (5) and conditional expression (5-1) to 1. For example, it is more preferable that the objective lens for an endoscope satisfies the following conditional expression (5-2).

$$0.5<fF/f1<1 \qquad (5-2)$$

It is preferable that the objective lens for an endoscope satisfies the following conditional expression (6). Since fF>0 and f2>0 are satisfied, a lower limit of conditional expression (6) is 0<fF/f2. By not allowing a corresponding value of conditional expression (6) to be equal to or greater than an upper limit value, it is advantageous in securing a favorable optical performance in observation over the entire range of an object distance from a farthest point to a nearest point.

$$0<fF/f2<0.5 \qquad (6)$$

In addition, it is preferable that the objective lens for an endoscope satisfies the following conditional expression (6-1). By not allowing a corresponding value of conditional expression (6-1) to be equal to or less than a lower limit value, there is an advantage in suppressing an increase in size of the lens system.

$$0.1<fF/f2<0.5 \qquad (6-1)$$

In order to obtain more favorable characteristics, it is more preferable to set upper limit values of conditional expression (6) and conditional expression (6-1) to 0.2. For example, it is more preferable that the objective lens for an endoscope satisfies the following conditional expression (6-2).

$$0.1<fF/f2<0.2 \qquad (6-2)$$

It is preferable that the objective lens for an endoscope satisfies the following conditional expression (7). An upper limit of conditional expression (7) is fL1/f1<0 since fL1<0 and f1>0 are satisfied. By not allowing a corresponding value of conditional expression (7) to be equal to or less than a lower limit value, there is an advantage in suppressing an increase in size of the lens system.

$$-1.5<fL1/f1<0 \qquad (7)$$

In addition, it is preferable that the objective lens for an endoscope satisfies the following conditional expression (7-1). By not allowing a corresponding value of conditional expression (7-1) to be equal to or greater than an upper limit value, it is advantageous in securing a favorable optical performance in observation over the entire range of an object distance from a farthest point to a nearest point.

$$-1.5<fL1/f1<-0.6 \qquad (7-1)$$

In order to obtain more favorable characteristics, it is more preferable to set lower limit values of conditional expression (7) and conditional expression (7-1) to −0.9. For example, it is more preferable that the objective lens for an endoscope satisfies the following conditional expression (7-2).

$$-0.9<fL1/f1<-0.6 \qquad (7-2)$$

In a configuration where the first lens group G1 consists of the first a lens group G1$a$ that has positive optical power, the aperture stop St, and the first b lens group G1$b$ that has positive optical power, in order from the object side to the image side, it is preferable that the objective lens for an endoscope satisfies at least one of the following conditional expression (8), (9), (10), or (11). Herein, a focal length of the first a lens group G1$a$ is f1a. A focal length of the first b lens group G1$b$ is f1b.

$$0<fF/f1a<1 \qquad (8)$$

$$0<f1/f1a<1 \qquad (9)$$

$$0<fF/f1b<1 \qquad (10)$$

$$0<f1/f1b<1 \qquad (11)$$

Since fF>0 and f1a>0 are satisfied, a lower limit of conditional expression (8) is 0<fF/f1a. By not allowing a corresponding value of conditional expression (8) to be equal to or greater than an upper limit value, it is advantageous in securing a favorable optical performance in observation over the entire range of an object distance from a farthest point to a nearest point.

In addition, it is preferable that the objective lens for an endoscope satisfies the following conditional expression (8-1). By not allowing a corresponding value of conditional expression (8-1) to be equal to or less than a lower limit value, there is an advantage in suppressing an increase in size of the lens system.

$$0.005<fF/f1a<1 \qquad (8-1)$$

In order to obtain more favorable characteristics, it is more preferable to set upper limit values of conditional expression (8) and conditional expression (8-1) to 0.6. For example, it is more preferable that the objective lens for an endoscope satisfies the following conditional expression (8-2).

$$0<fF/f1a<0.6 \qquad (8-2)$$

Since f1>0 and f1a>0 are satisfied, a lower limit of conditional expression (9) is 0<f1/f1a. By not allowing a corresponding value of conditional expression (9) to be equal to or greater than an upper limit value, it is advantageous in securing a favorable optical performance in observation over the entire range of an object distance from a farthest point to a nearest point.

In addition, it is preferable that the objective lens for an endoscope satisfies the following conditional expression (9-1). By not allowing a corresponding value of conditional expression (9-1) to be equal to or less than a lower limit value, there is an advantage in suppressing an increase in size of the lens system.

$$0.005<f1/f1a<1 \qquad (9-1)$$

In order to obtain more favorable characteristics, it is more preferable to set upper limit values of conditional expression (9) and conditional expression (9-1) to 0.7. For example, it is more preferable that the objective lens for an endoscope satisfies the following conditional expression (9-2).

$$0 < f1/f1a < 0.7 \qquad (9-2)$$

Since fF>0 and f1b>0 are satisfied, a lower limit of conditional expression (10) is 0<fF/f1b. By not allowing a corresponding value of conditional expression (10) to be equal to or greater than an upper limit value, it is advantageous in securing a favorable optical performance in observation over the entire range of an object distance from a farthest point to a nearest point.

In addition, it is preferable that the objective lens for an endoscope satisfies the following conditional expression (10-1). By not allowing a corresponding value of conditional expression (10-1) to be equal to or less than a lower limit value, there is an advantage in suppressing an increase in size of the lens system.

$$0.1 < fF/f1b < 1 \qquad (10-1)$$

In order to obtain more favorable characteristics, it is more preferable to set upper limit values of conditional expression (10) and conditional expression (10-1) to 0.3. For example, it is more preferable that the objective lens for an endoscope satisfies the following conditional expression (10-2).

$$0.1 < fF/f1b < 0.3 \qquad (10-2)$$

Since f1>0 and f1b>0 are satisfied, a lower limit of conditional expression (11) is 0<f1/f1b. By not allowing a corresponding value of conditional expression (11) to be equal to or greater than an upper limit value, it is advantageous in securing a favorable optical performance in observation over the entire range of an object distance from a farthest point to a nearest point.

In addition, it is preferable that the objective lens for an endoscope satisfies the following conditional expression (11-1). By not allowing a corresponding value of conditional expression (11-1) to be equal to or less than a lower limit value, there is an advantage in suppressing an increase in size of the lens system.

$$0.1 < f1/f1b < 1 \qquad (11-1)$$

In order to obtain more favorable characteristics, it is more preferable to set upper limit values of conditional expression (11) and conditional expression (11-1) to 0.4. For example, it is more preferable that the objective lens for an endoscope satisfies the following conditional expression (11-2).

$$0.1 < f1/f1b < 0.4 \qquad (11-2)$$

It is preferable that the objective lens for an endoscope satisfies the following conditional expression (13) in a configuration where the first lens group G1 consists of, in order from the object side to the image side, the first a lens group G1a that has positive optical power, the aperture stop St, and the first b lens group G1b that has positive optical power, and the first a lens group G1a includes a cemented lens in which at least one negative lens and at least one positive lens are cemented. Herein, an average value of Abbe numbers of all the positive lenses included in the cemented lens of the first a lens group G1a based on a d line is ν1p. An average value of Abbe numbers of all the negative lenses included in the cemented lens of the first a lens group G1a based on the d line is ν1n. Since |ν1p−ν1n| is an absolute value, a lower limit of conditional expression (13) is 0<|ν1p−ν1n|. By not allowing a corresponding value of conditional expression (13) to be equal to or greater than an upper limit value, excessive increases in correction amounts of axial chromatic aberration and lateral chromatic aberration can be suppressed. Thus, there is an advantage in optimally controlling axial chromatic aberration and lateral chromatic aberration.

$$0 < |ν1p−ν1n| < 40 \qquad (13)$$

In addition, it is preferable that the objective lens for an endoscope satisfies the following conditional expression (13-1). By not allowing a corresponding value of conditional expression (13-1) to be equal to or less than a lower limit value, there is an advantage in suppressing longitudinal chromatic aberration and lateral chromatic aberration from a visible region to a short wavelength region near a wavelength of 400 nm.

$$5.5 < |ν1p−ν1n| < 40 \qquad (13-1)$$

In order to obtain more favorable characteristics, it is more preferable to set upper limit values of conditional expression (13) and conditional expression (13-1) to 37. For example, it is more preferable that the objective lens for an endoscope satisfies the following conditional expression (13-2).

$$5.5 < |ν1p−ν1n| < 37 \qquad (13-2)$$

In a configuration where the second lens group G2 includes a cemented lens in which at least one positive lens and at least one negative lens are cemented, it is preferable that the objective lens for an endoscope satisfies the following conditional expression (14). Herein, an average value of Abbe numbers of all the positive lenses included in the cemented lens of the second lens group G2 based on the d line is ν2p. An average value of Abbe numbers of all the negative lenses included in the cemented lens of the second lens group G2 based on the d line is ν2n. By not allowing a corresponding value of conditional expression (14) to be equal to or less than a lower limit value, there is an advantage in suppressing longitudinal chromatic aberration and lateral chromatic aberration from a visible region to a short wavelength region near a wavelength of 400 nm. By not allowing a corresponding value of conditional expression (14) to be equal to or greater than an upper limit value, excessive increases in correction amounts of axial chromatic aberration and lateral chromatic aberration can be suppressed. Thus, there is an advantage in optimally controlling axial chromatic aberration and lateral chromatic aberration.

$$25 < |ν2p−ν2n| < 85 \qquad (14)$$

In order to obtain more favorable characteristics, it is more preferable to set a lower limit value of conditional expression (14) to 26. In addition, it is preferable to set an upper limit value of conditional expression (14) to 70. For example, it is more preferable that the objective lens for an endoscope satisfies the following conditional expression (14-1).

$$26 < |ν2p−ν2n| < 70 \qquad (14-1)$$

It is preferable that the objective lens for an endoscope satisfies the following conditional expression (12). Herein, a distance by which the second lens group G2 moves during focusing from a farthest point object to a nearest point object is M. A paraxial imaging magnification of the whole system in a state where the farthest point object is in focus is βf. A paraxial imaging magnification of the whole system in a state where the nearest point object is in focus is βn. A lateral magnification is used as βf and βn instead of a vertical magnification. For example, FIG. 1 shows the distance M. By not allowing a corresponding value of conditional expression (12) to be equal to or less than a lower limit value, there is an advantage in suppressing an increase in size of the lens system. By not allowing a corresponding value of conditional expression (12) to be equal to or greater than an upper limit value, an increase in sensitivity of focusing in a case where the second lens group G2 moves can be suppressed. Therefore, there is an advantage in achieving ease in focusing.

$$0.01 < (fF/|M|) \times (\beta f/\beta n) < 1 \tag{12}$$

In order to obtain more favorable characteristics, it is more preferable to set a lower limit value of conditional expression (12) to 0.15. In addition, it is preferable to set an upper limit value of conditional expression (12) to 0.5. For example, it is more preferable that the objective lens for an endoscope satisfies the following conditional expression (12-1).

$$0.15 < (fF/|M|) \times (\beta f/\beta n) < 0.5 \tag{12-1}$$

The example shown in FIG. 1 is an example, and various modifications can be made without departing from the scope of the technique according to the embodiment of the present disclosure. For example, the number of lenses included in each lens group may be different from the number in the example of FIG. 1. In addition, configurations of lenses included in each lens group can be different from the configurations in the example in FIG. 1.

For example, the first a lens group G1a may be configured to include, in order from the object side to the image side, a single lens that has negative optical power and that has a plane facing the object side, a negative lens, and a positive single lens. Alternatively, the first a lens group G1a may be configured to include, in order from the object side to the image side, a single lens that has negative optical power and that has a plane facing the object side, a single lens that has positive optical power, a negative lens, and a positive single lens. In a case where the first a lens group G1a includes a cemented lens in which at least one negative lens and at least one positive lens are cemented, the cemented lens may be disposed adjacent to the object side of the aperture stop St.

The first b lens group G1b may be configured to consist of, in order from the object side to the image side, a positive lens and a negative lens. In this case, the positive lens and the negative lens of the first b lens group G1b may be cemented to each other. The first b lens group G1b may be configured to consist of one cemented lens. Alternatively, the first b lens group G1b may be configured to consist of one positive lens.

The second lens group G2 may be configured to consist of a cemented lens in which a negative lens and a positive lens are cemented in order from the object side. Alternatively, the second lens group G2 may be configured to consist of a cemented lens in which a positive lens and a negative lens are cemented in order from the object side.

The preferable configurations and available configurations described above, also including configurations related to conditional expressions, may be optionally combined without contradiction, and it is preferable to selectively adopt configurations in accordance with required specifications as appropriate.

For example, in one preferable aspect of the objective lens for an endoscope according to the embodiment of the present disclosure, the objective lens consists of the first lens group G1 that has positive optical power and the second lens group G2 that has positive optical power, in order from the object side to the image side, during focusing from a farthest point object to a nearest point object, the first lens group G1 is fixed to the image plane Sim, only the second lens group G2 moves along the optical axis Z, the first lens group G1 includes a single lens that has negative optical power closest to the object side, and conditional expressions (1), (2), and (3) are satisfied.

Next, examples of the objective lens for an endoscope according to the embodiment of the present disclosure will be described with reference to the drawings. A reference numeral assigned to each lens and each group in a cross-sectional view of each example is independently used for each example in order to avoid complication of description and drawings caused by an increase in the number of digits of the reference numerals. Therefore, even in a case where common reference numerals are assigned in the drawings of different examples, common reference numerals do not necessarily indicate common configurations.

Example 1

Since a cross-sectional view showing a configuration of an objective lens for an endoscope of example 1 is shown in FIGS. 1 and 2, a showing method thereof is as described above, and repeated description thereof will be partially omitted herein. The objective lens for an endoscope of example 1 consists of the first lens group G1 that has positive optical power and the second lens group G2 that has positive optical power, in order from the object side to the image side. During focusing from the farthest point object to the nearest point object, the first lens group G1 is fixed to the image plane Sim, and the second lens group G2 moves to the object side. The first lens group G1 consists of, in order from the object side to the image side, the first a lens group G1a that has positive optical power, the aperture stop St, and the first b lens group G1b that has positive optical power. The outline of the objective lens for an endoscope of example 1 is as described above.

Each group of the objective lens for an endoscope of example 1 is composed as follows. The first a lens group G1a consists of the lens L11, the optical member P1, the lens L12, and the lens L13, in order from the object side to the image side. The first b lens group G1b consists of the lens L14 and the lens L15, in order from the object side to the image side. The second lens group G2 consists of the lens L21 and the lens L22, in order from the object side to the image side. The lens L12 and the lens L13 are cemented to each other. The lens L14 and the lens L15 are cemented to each other. The lens L21 and the lens L22 are cemented to each other. The lens L11 is a single lens.

Basic lens data of the objective lens for an endoscope of example 1 is shown in table 1, and specifications and variable surface spacing thereof are shown in table 2.

The table of basic lens data will be described as follows. The "Sn" column shows surface numbers in a case where a surface closest to the object side is a first surface and the number is increased one by one toward the image side. The "R" column shows a curvature radius of each surface. The "D" column shows surface spacing on the optical axis between each surface and the surface adjacent to the image side. The "Nd" column shows a refractive index of each lens with respect to the d line. The "vd" column shows the Abbe number of each lens based on the d line.

In the table of basic lens data, the reference numeral of the curvature radius of a surface convex toward the object side is positive, and the reference numeral of the curvature radius of a surface convex toward the image side is negative. In table 1, a field of the surface number of the surface corresponding to the aperture stop St has a surface number and a text (St). Table 1 also shows the optical member PP. A value in the bottom field of the column of D in the table is spacing between the surface closest to the image side and the image plane Sim in the table. A symbol DD[ ] is used for variable surface spacing during focusing. A surface number on the object side of the spacing is provided inside [ ] and is shown in the column of the surface spacing.

In table 2, for the farthest point observation state and the nearest point observation state, each of values of a focal length, a back focus at an air conversion distance, an F-number, a maximum total angle of view, a maximum image height, an object distance, a paraxial imaging magnification, and variable surface spacing is shown. The object distance is a distance on the optical axis from an object to the lens surface closest to the object side in the first lens group G1. [°] in the field of the maximum total angle of view shows the unit, which is degrees. Values shown in table 2 are based on the d line.

In the data of each table, degrees are used as the unit of an angle, and millimeters (mm) are used as the unit of a length, but appropriate different units can be used since the optical system can be used even in a case where the optical system is enlarged or reduced in proportion. In addition, numerical values rounded to digits determined in advance are shown in each table shown below.

TABLE 1

| | | Example 1 | | |
| --- | --- | --- | --- | --- |
| Sn | R | D | Nd | vd |
| 1 | ∞ | 0.2500 | 2.00100 | 29.13 |
| 2 | 0.6100 | 0.3200 | | |
| 3 | ∞ | 0.3000 | 1.51633 | 64.14 |
| 4 | ∞ | 0.3700 | | |
| 5 | ∞ | 0.2600 | 1.59522 | 67.73 |
| 6 | 0.7062 | 0.7400 | 1.68893 | 31.07 |
| 7 | −1.4691 | 0.1550 | | |
| 8(St) | ∞ | 0.1050 | | |
| 9 | ∞ | 0.5700 | 1.69680 | 55.53 |
| 10 | −0.5775 | 0.2500 | 2.00069 | 25.46 |
| 11 | −1.3023 | DD[11] | | |
| 12 | 9.9601 | 0.2500 | 2.00069 | 25.46 |
| 13 | 1.9932 | 0.7200 | 1.43875 | 94.66 |
| 14 | −1.3023 | DD[14] | | |
| 15 | ∞ | 1.8400 | 1.88299 | 40.78 |
| 16 | ∞ | 0.1500 | 1.51633 | 64.06 |
| 17 | ∞ | 0.0100 | | |

TABLE 2

| | Example 1 | |
| --- | --- | --- |
| | Farthest point observation state | Nearest point observation state |
| Focal length | 0.695 | 0.661 |
| Back focus | 1.491 | 1.705 |
| F-number | 4.01 | 3.91 |
| Maximum total angle of view [°] | 137.7 | 143.4 |
| Maximum image height | 0.675 | 0.675 |
| Object distance | 20.00 | 2.25 |
| Paraxial imaging magnification | −0.0340 | −0.2428 |
| DD[11] | 0.5400 | 0.1892 |
| DD[14] | 0.4288 | 0.7796 |

Figure 3:
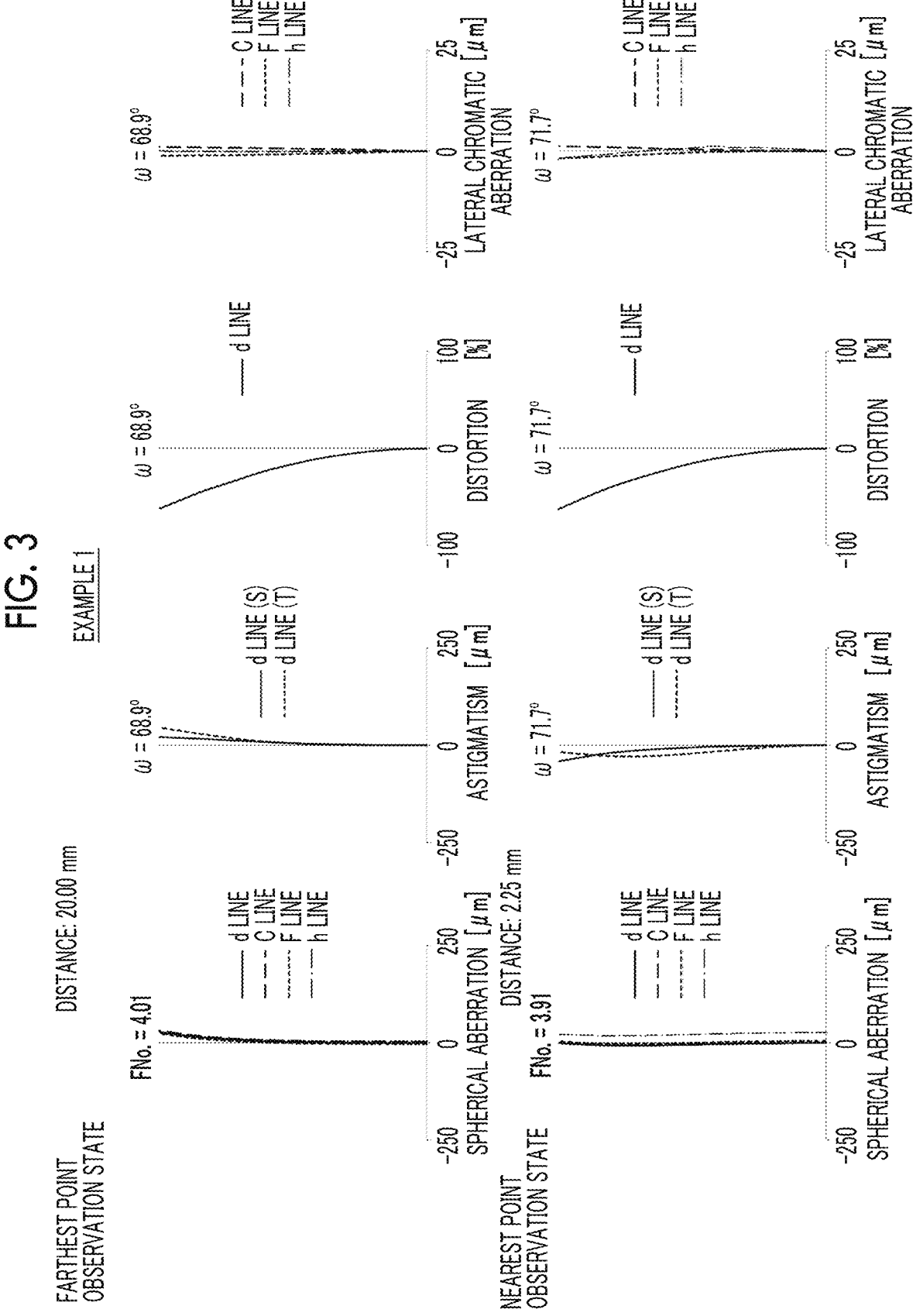
FIG. 3 is each aberration diagram of the objective lens for an endoscope of example 1.

FIG. 3 shows each aberration diagram of the objective lens for an endoscope of example 1. A spherical aberration diagram, an astigmatism diagram, a distortion diagram, and a lateral chromatic aberration diagram are shown in FIG. 3 in this order from the left. In FIG. 3, each of the aberration diagrams of the farthest point observation state is shown in the upper part, and each of the aberration diagrams of the nearest point observation state is shown in the lower part. In FIG. 3, a value of the object distance is shown on the right of "distance:". In the spherical aberration diagram, aberrations with respect to the d line, a C line, an F line, and an h line are shown by a solid line, a long broken line, a short broken line, and a one-dot chain line, respectively. In the astigmatism diagram, aberration in a sagittal direction with respect to the d line is shown by a solid line, and aberration in a tangential direction with respect to the d line is shown by a short broken line. In the distortion diagram, aberration with respect to the d line is shown by a solid line. In the lateral chromatic aberration diagram, aberrations with respect to the C line, the F line, and the h line are shown by a long broken line, a short broken line, and a one-dot chain line, respectively. In the spherical aberration diagram, a value of the F-number in each state is shown after "FNo.=". In other aberration diagrams, a value of the maximum half angle of view in each state is shown after "@=".

Symbols, meanings, description methods, and showing methods of each piece of data related to example 1 are the same as those in the following examples unless stated otherwise. Thus, hereinafter, redundant description will be omitted.

Example 2

Figure 4:
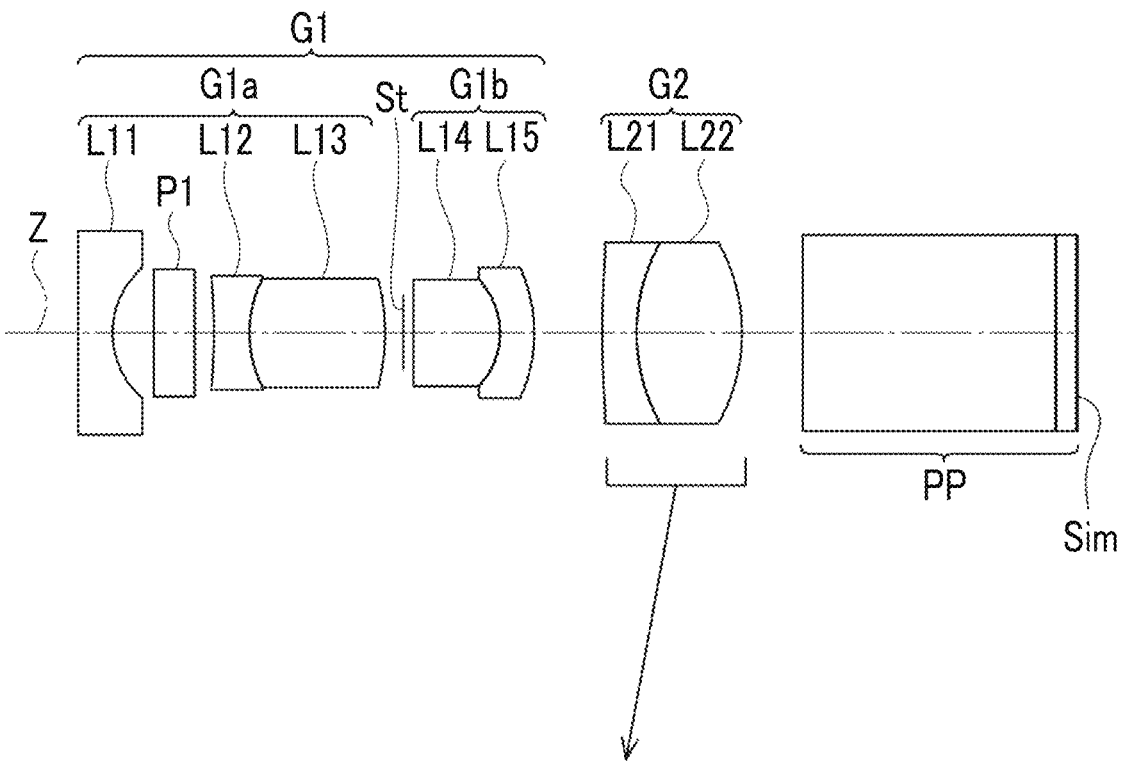
FIG. 4 is a cross-sectional view showing a configuration of an objective lens for an endoscope of example 2.
Figure 4:
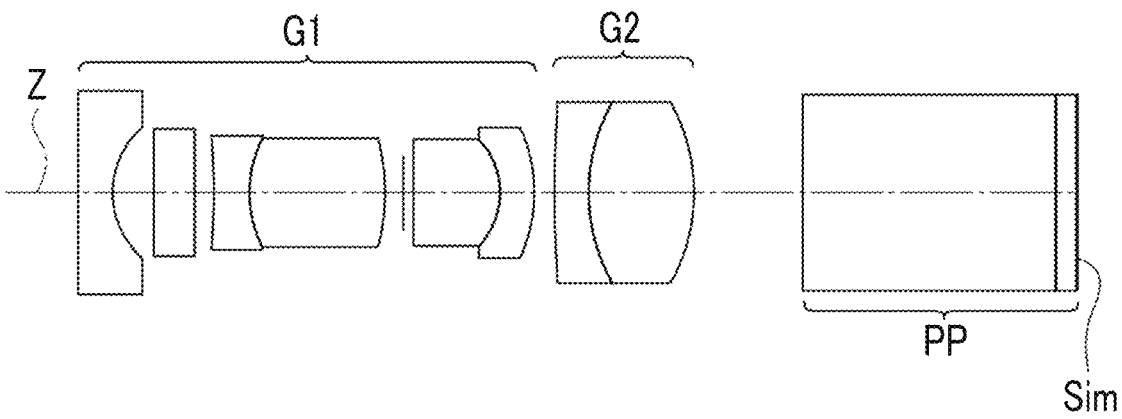

A cross-sectional view showing a configuration of an objective lens for an endoscope of example 2 is shown in FIG. 4. The objective lens for an endoscope of example 2 has the same configuration as the outline of the objective lens for an endoscope of example 1.

Each group of the objective lens for an endoscope of example 2 is composed as follows. The first a lens group G1a consists of the lens L11, the optical member P1, the lens L12, and the lens L13, in order from the object side to the image side. The first b lens group G1b consists of the lens L14 and the lens L15, in order from the object side to the image side. The second lens group G2 consists of the lens L21 and the lens L22, in order from the object side to the image side. The lens L12 and the lens L13 are cemented to each other. The lens L14 and the lens L15 are cemented to each other. The lens L21 and the lens L22 are cemented to each other. The lens L11 is a single lens.

Figure 5:
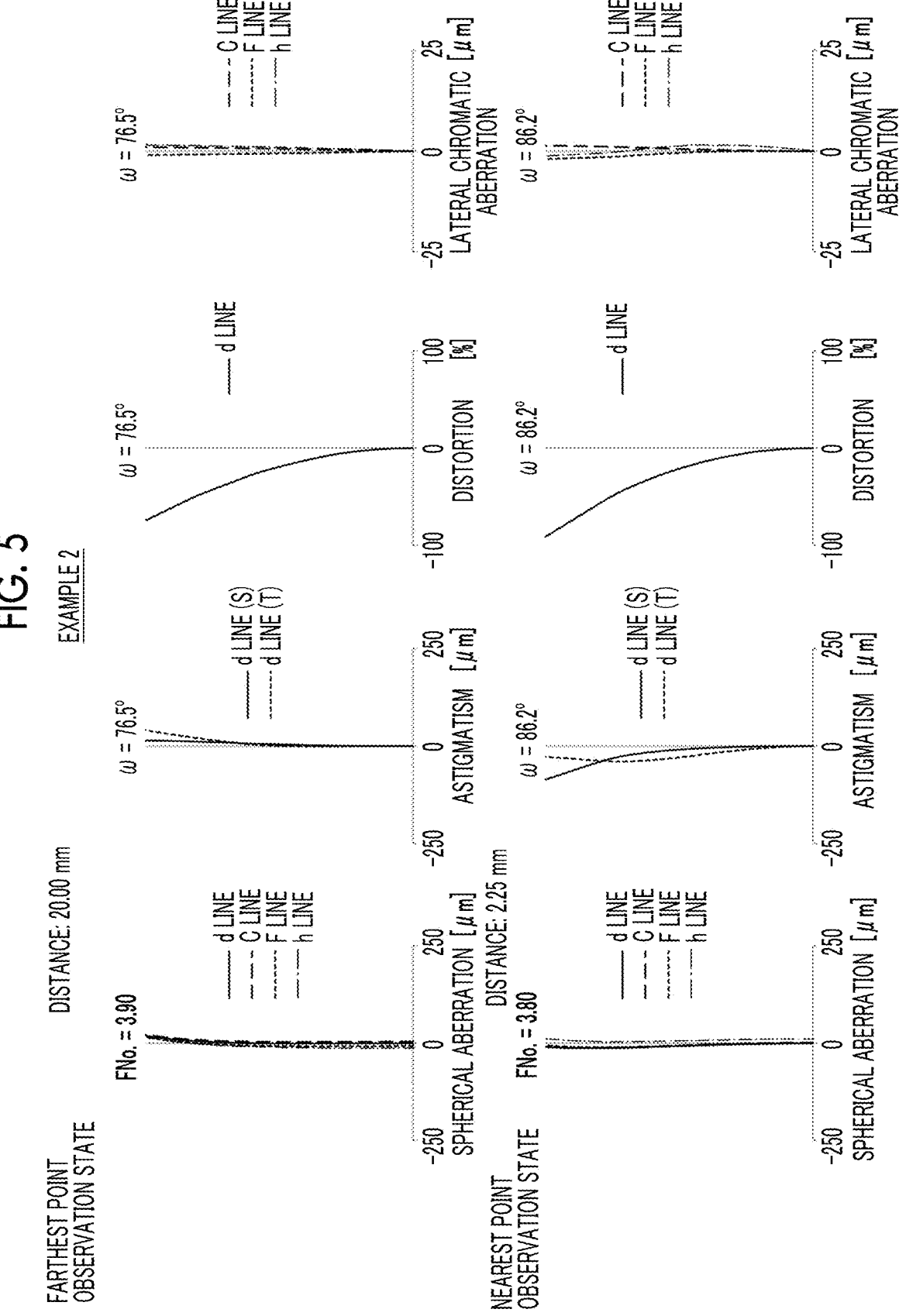
FIG. 5 is each aberration diagram of the objective lens for an endoscope of example 2.

Basic lens data of the objective lens for an endoscope of example 2 is shown in table 3, specifications and variable surface spacing thereof are shown in table 4, and each aberration diagram thereof is shown in FIG. 5.

TABLE 3

| | | Example 2 | | |
| --- | --- | --- | --- | --- |
| Sn | R | D | Nd | vd |
| 1 | ∞ | 0.2500 | 2.00100 | 29.13 |
| 2 | 0.6442 | 0.3000 | | |
| 3 | ∞ | 0.3000 | 1.51633 | 64.14 |
| 4 | ∞ | 0.1400 | | |
| 5 | −4.6681 | 0.2600 | 1.69680 | 55.53 |
| 6 | 0.8922 | 0.9900 | 1.80518 | 25.42 |
| 7 | 1.5928 | 0.1350 | | |
| 8(St) | ∞ | 0.0750 | | |
| 9 | ∞ | 0.6300 | 1.69680 | 55.53 |
| 10 | −0.5775 | 0.2500 | 2.00069 | 25.46 |
| 11 | −1.1757 | DD[11] | | |

TABLE 3-continued

| | Example 2 | | | |
|---|---|---|---|---|
| Sn | R | D | Nd | νd |
| 12 | 8.3054 | 0.2500 | 2.00069 | 25.46 |
| 13 | 1.3800 | 0.7700 | 1.51742 | 52.43 |
| 14 | −1.3800 | DD[14] | | |
| 15 | ∞ | 1.8500 | 1.88299 | 40.78 |
| 16 | ∞ | 0.1500 | 1.51633 | 64.06 |
| 17 | ∞ | 0.0100 | | |

TABLE 4

| | Example 2 | |
|---|---|---|
| | Farthest point | Nearest point |
| Focal length | 0.678 | 0.643 |
| Back focus | 1.511 | 1.732 |
| F-number | 3.90 | 3.80 |
| Maximum total angle of view [°] | 153.0 | 172.4 |
| Maximum image height | 0.710 | 0.710 |
| Object distance | 20.00 | 2.25 |
| Paraxial imaging magnification | −0.0331 | −0.2358 |
| DD[11] | 0.4900 | 0.1398 |
| DD[14] | 0.4422 | 0.7924 |

Example 3

Figure 6:
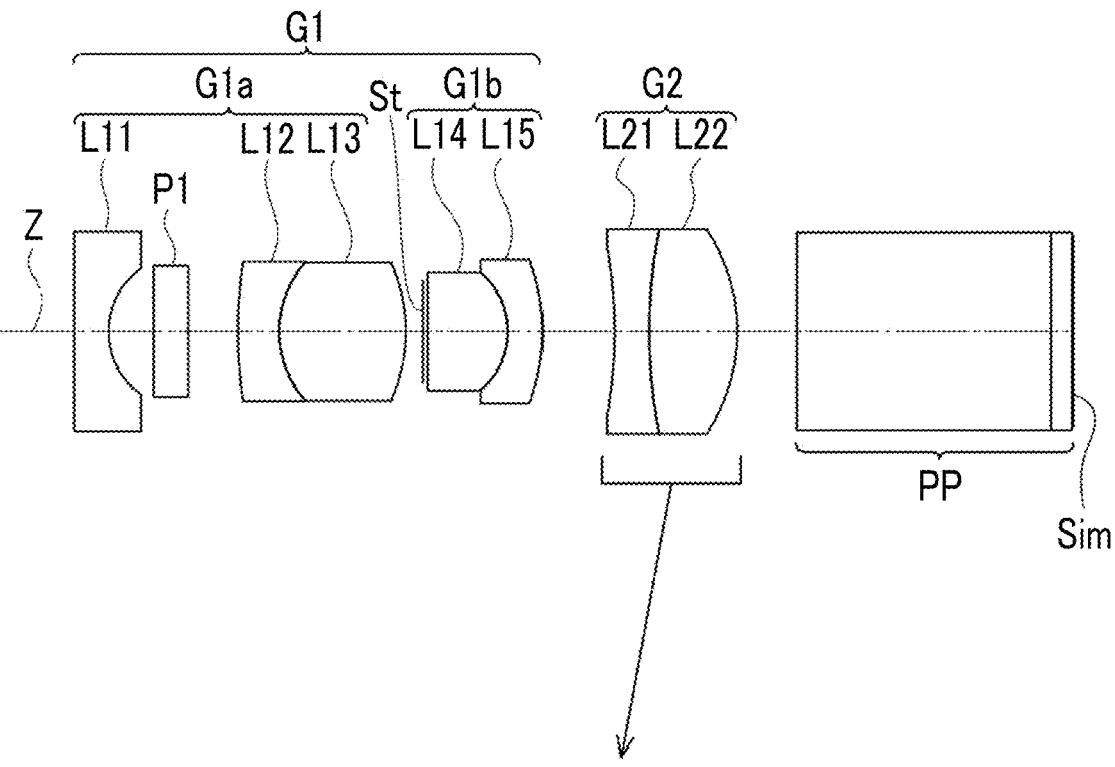
FIG. 6 is a cross-sectional view showing a configuration of an objective lens for an endoscope of example 3.
Figure 6:
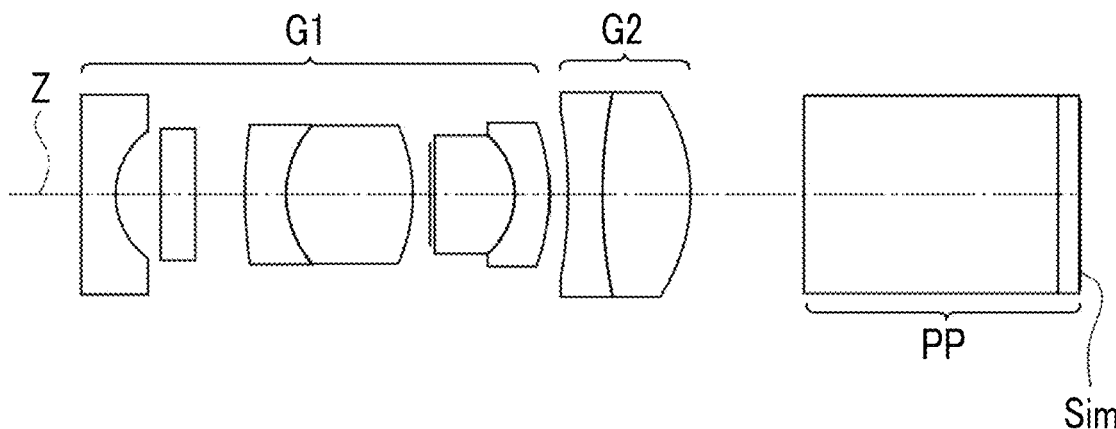

A cross-sectional view showing a configuration of an objective lens for an endoscope of example 3 is shown in FIG. 6. The objective lens for an endoscope of example 3 has the same configuration as the outline of the objective lens for an endoscope of example 1. Each group of the objective lens for an endoscope of example 3 is composed as follows.

The first a lens group G1a consists of the lens L11, the optical member P1, the lens L12, and the lens L13, in order from the object side to the image side. The first b lens group G1b consists of the lens L14 and the lens L15, in order from the object side to the image side. The second lens group G2 consists of the lens L21 and the lens L22, in order from the object side to the image side. The lens L12 and the lens L13 are cemented to each other. The lens L14 and the lens L15 are cemented to each other. The lens L21 and the lens L22 are cemented to each other. The lens L11 is a single lens.

Figure 7:
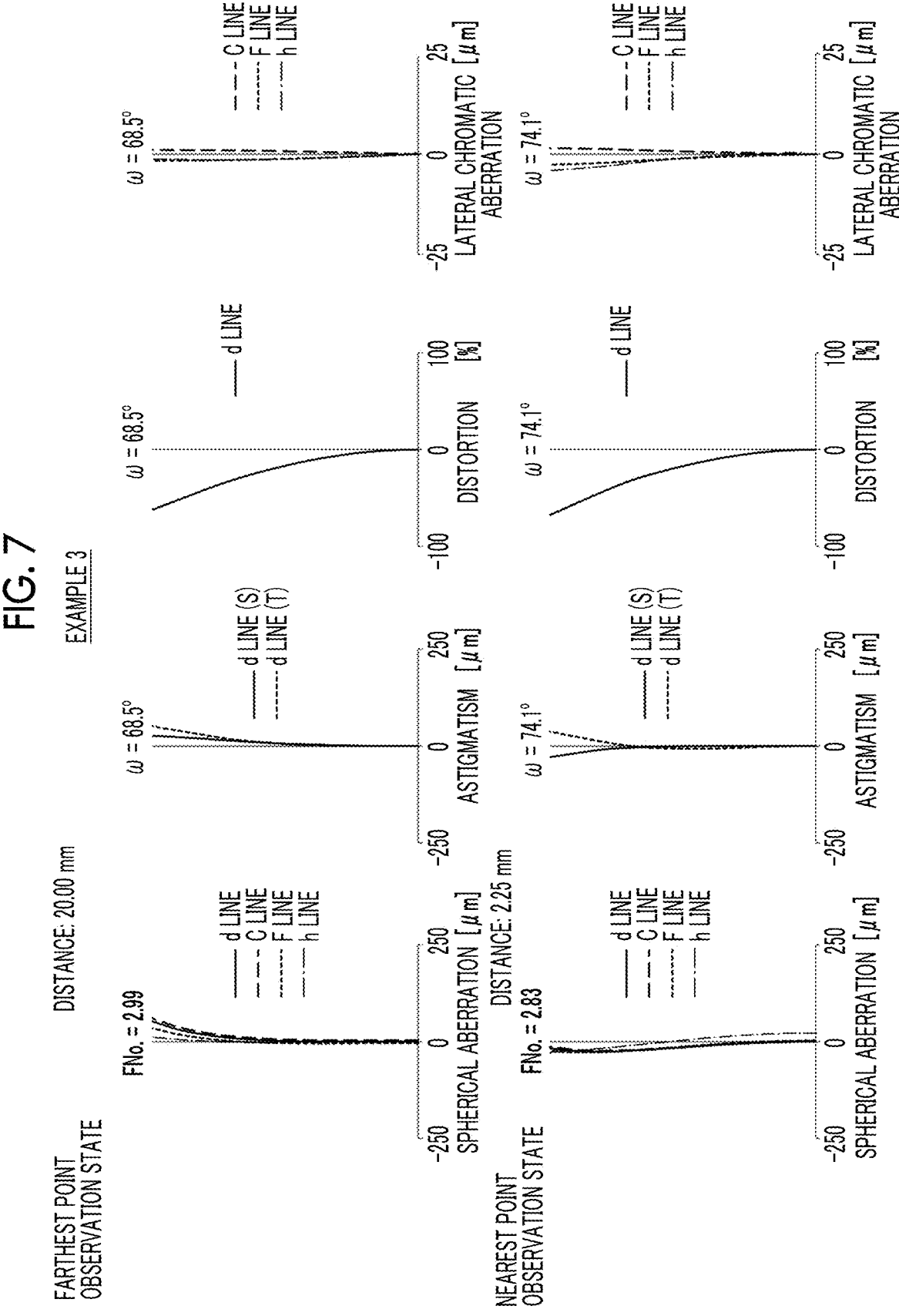
FIG. 7 is each aberration diagram of the objective lens for an endoscope of example 3.

Basic lens data of the objective lens for an endoscope of example 3 is shown in table 5, specifications and variable surface spacing thereof are shown in table 6, and each aberration diagram thereof is shown in FIG. 7.

TABLE 5

| | Example 3 | | | |
|---|---|---|---|---|
| Sn | R | D | Nd | νd |
| 1 | ∞ | 0.2500 | 2.00100 | 29.13 |
| 2 | 0.5775 | 0.3300 | | |
| 3 | ∞ | 0.2500 | 2.00100 | 29.13 |
| 4 | ∞ | 0.3600 | | |
| 5 | 3.5051 | 0.3000 | 1.59522 | 67.73 |
| 6 | 0.7768 | 0.9200 | 1.68893 | 31.07 |
| 7 | −1.2496 | 0.1250 | | |
| 8(St) | ∞ | 0.0350 | | |
| 9 | ∞ | 0.5800 | 1.69680 | 55.53 |
| 10 | −0.5775 | 0.2500 | 2.00069 | 25.46 |
| 11 | −1.5391 | DD[11] | | |

TABLE 5-continued

| | Example 3 | | | |
|---|---|---|---|---|
| Sn | R | D | Nd | νd |
| 12 | −3.5051 | 0.2500 | 2.00069 | 25.46 |
| 13 | 3.8959 | 0.6400 | 1.69680 | 55.53 |
| 14 | −1.3800 | DD[14] | | |
| 15 | ∞ | 1.8500 | 1.88299 | 40.78 |
| 16 | ∞ | 0.1500 | 1.51633 | 64.06 |
| 17 | ∞ | 0.0100 | | |

TABLE 6

| | Example 3 | |
|---|---|---|
| | Farthest point | Nearest point |
| Focal length | 0.711 | 0.662 |
| Back focus | 1.499 | 1.751 |
| F-number | 2.99 | 2.83 |
| Maximum total angle of view [°] | 137.0 | 148.3 |
| Maximum image height | 0.675 | 0.675 |
| Object distance | 20.00 | 2.25 |
| Paraxial imaging magnification | −0.0347 | −0.2441 |
| DD[11] | 0.5200 | 0.1304 |
| DD[14] | 0.4319 | 0.8215 |

Example 4

Figure 8:
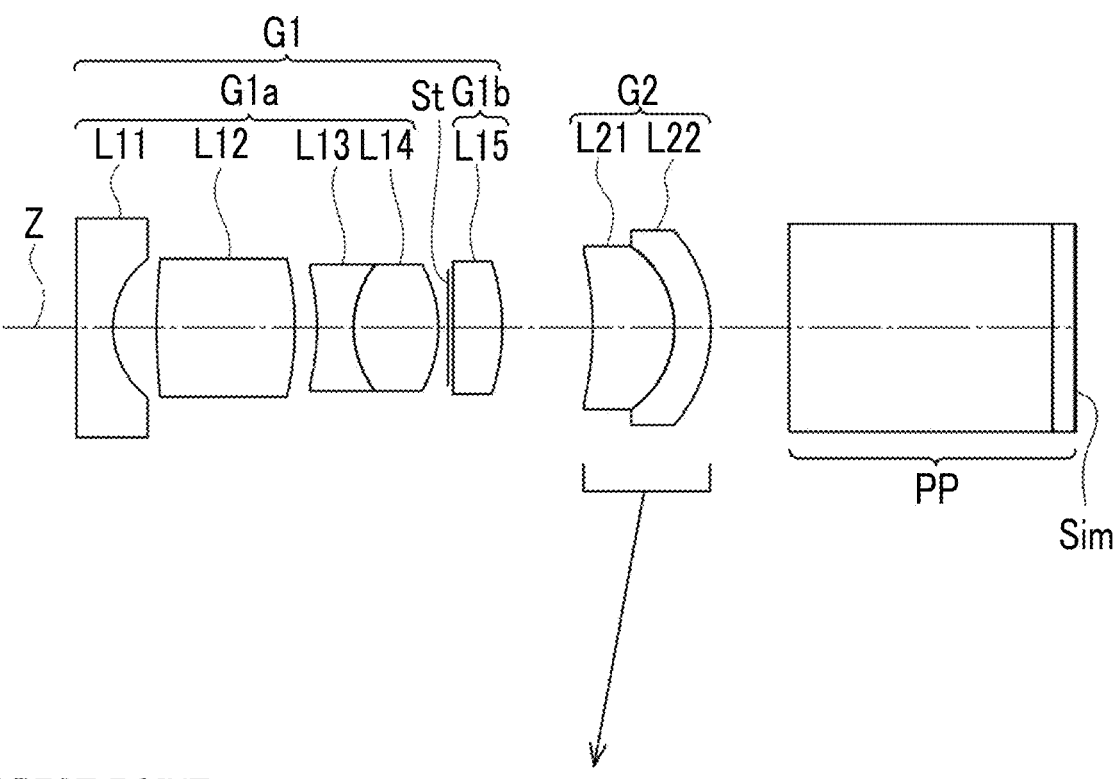
FIG. 8 is a cross-sectional view showing a configuration of an objective lens for an endoscope of example 4.
Figure 8:
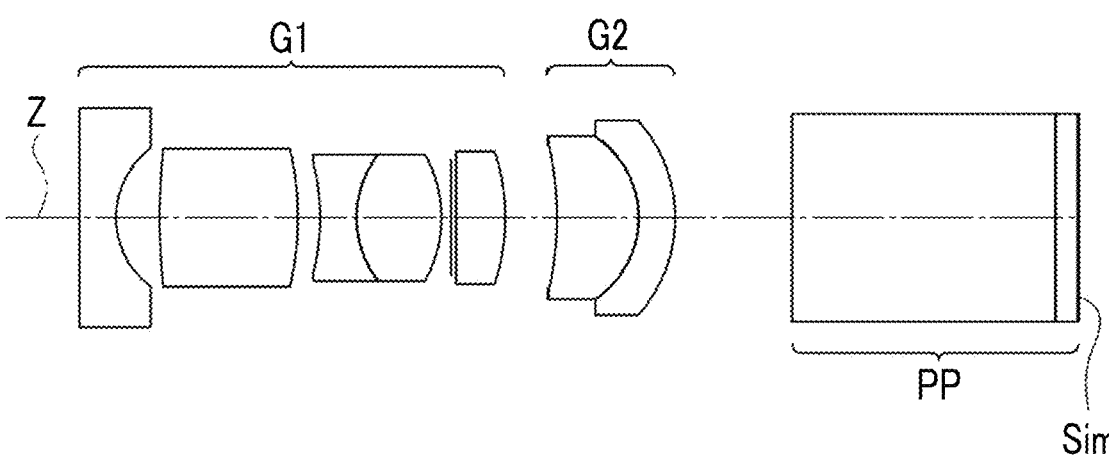

A cross-sectional view showing a configuration of an objective lens for an endoscope of example 4 is shown in FIG. 8. The objective lens for an endoscope of example 4 has the same configuration as the outline of the objective lens for an endoscope of example 1.

Each group of the objective lens for an endoscope of example 4 is composed as follows. The first a lens group G1a consists of the lens L11, the lens L12, the lens L13, and the lens L14 in order from the object side to the image side. The first b lens group G1b consists of the lens L15. The second lens group G2 consists of the lens L21 and the lens L22, in order from the object side to the image side. The lens L13 and the lens L14 are cemented to each other. The lens L21 and the lens L22 are cemented to each other. Each of the lens L11, the lens L12, and the lens L15 is a single lens.

Figure 9:
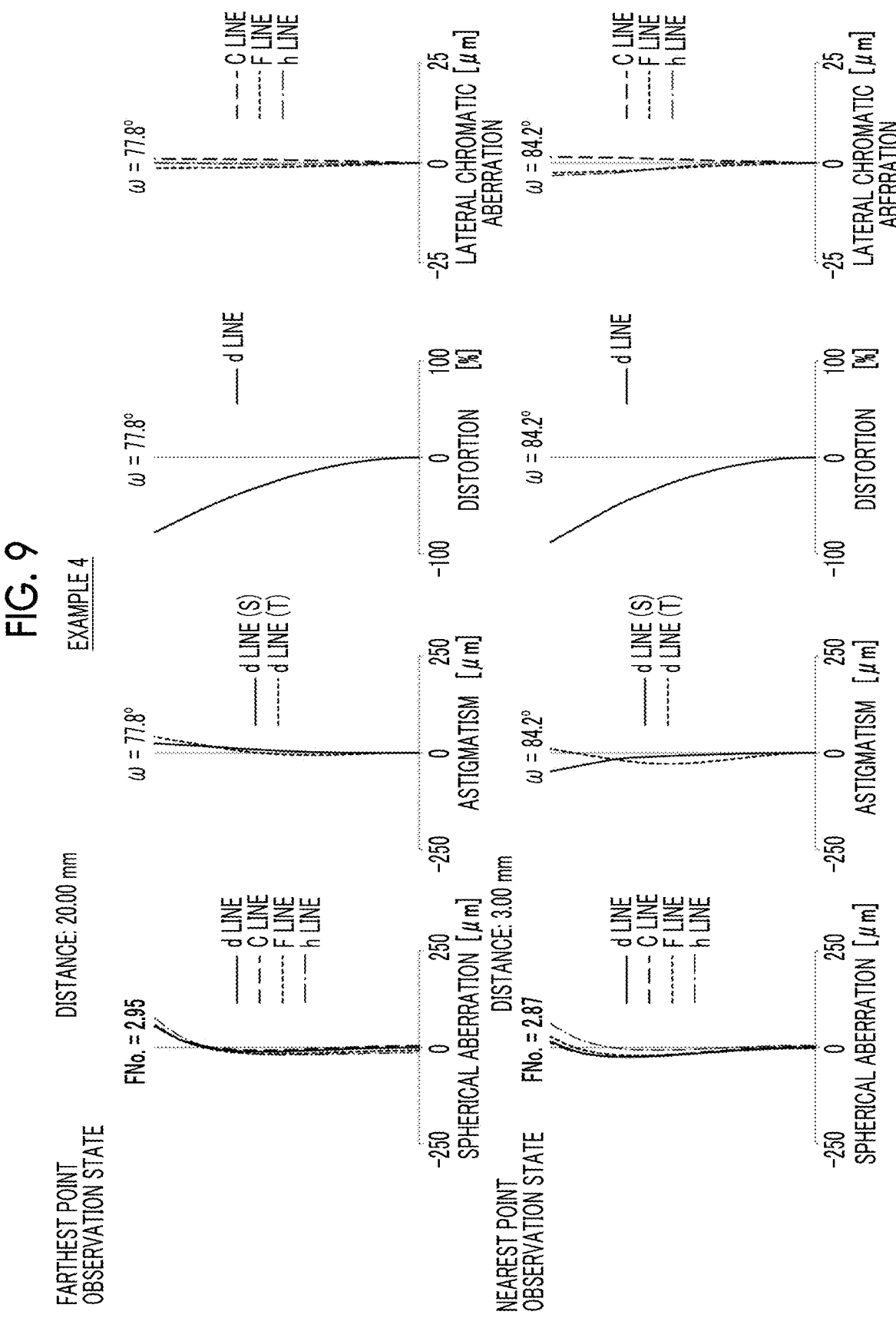
FIG. 9 is each aberration diagram of the objective lens for an endoscope of example 4.

Basic lens data of the objective lens for an endoscope of example 4 is shown in table 7, specifications and variable surface spacing thereof are shown in table 8, and each aberration diagram thereof is shown in FIG. 9.

TABLE 7

| | Example 4 | | | |
|---|---|---|---|---|
| Sn | R | D | Nd | νd |
| 1 | ∞ | 0.2500 | 2.00100 | 29.13 |
| 2 | 0.6007 | 0.2986 | | |
| 3 | 4.6684 | 0.9452 | 1.94595 | 17.98 |
| 4 | −2.1032 | 0.1514 | | |
| 5 | −1.6042 | 0.2500 | 1.95375 | 32.32 |
| 6 | 0.7224 | 0.5800 | 1.72342 | 37.95 |
| 7 | 0.9017 | 0.0650 | | |
| 8(St) | ∞ | 0.0350 | | |
| 9 | ∞ | 0.3370 | 1.43875 | 94.66 |
| 10 | −1.4693 | DD[10] | | |
| 11 | −2.2858 | 0.5585 | 1.53775 | 74.70 |
| 12 | −0.6823 | 0.2500 | 1.94595 | 17.98 |

TABLE 7-continued

| | | Example 4 | | |
|---|---|---|---|---|
| Sn | R | D | Nd | νd |
| 13 | −1.0154 | DD[13] | | |
| 14 | ∞ | 1.8000 | 1.55919 | 53.90 |
| 15 | ∞ | 0.1500 | 1.51633 | 64.06 |
| 16 | ∞ | 0.0100 | | |

TABLE 8

| | Example 4 | |
|---|---|---|
| | Farthest point | Nearest point |
| Focal length | 0.713 | 0.680 |
| Back focus | 1.774 | 1.931 |
| F-number | 2.95 | 2.87 |
| Maximum total angle of view [°] | 155.6 | 168.5 |
| Maximum image height | 0.715 | 0.715 |
| Object distance | 20.00 | 3.00 |
| Paraxial imaging magnification | −0.0348 | −0.1962 |
| DD[10] | 0.6113 | 0.3464 |
| DD[13] | 0.5357 | 0.8006 |

Example 5

Figure 10:
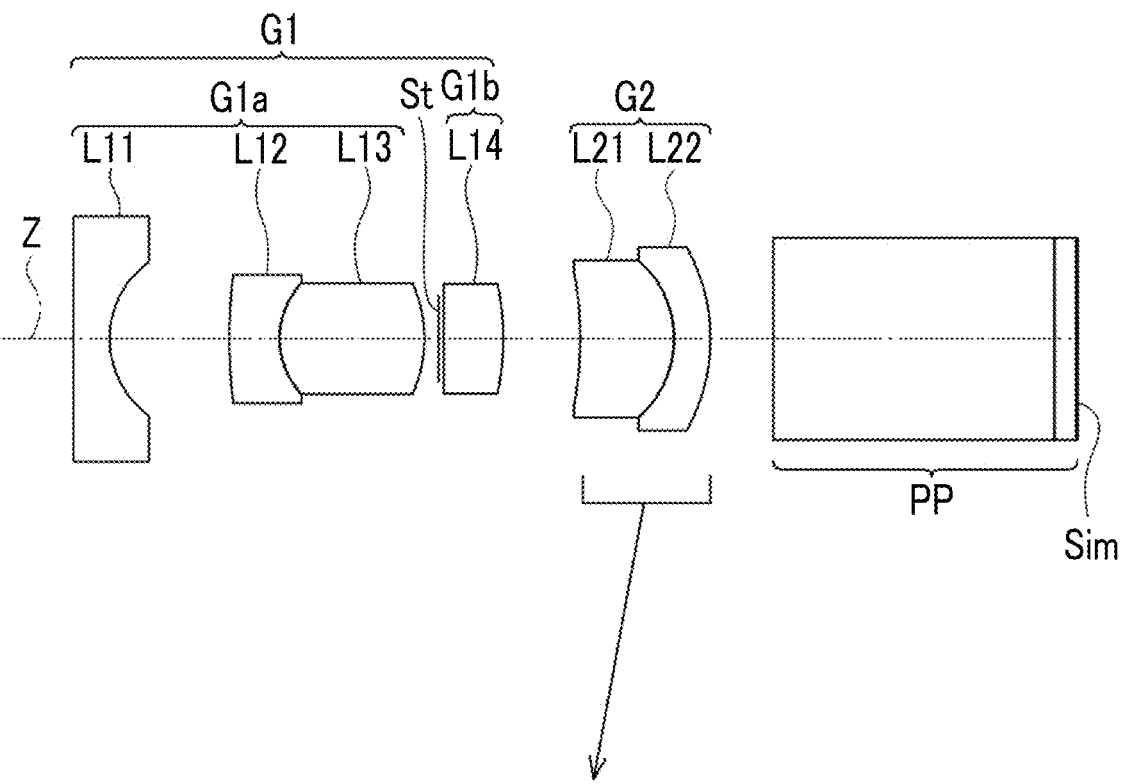
FIG. 10 is a cross-sectional view showing a configuration of an objective lens for an endoscope of example 5.
Figure 10:
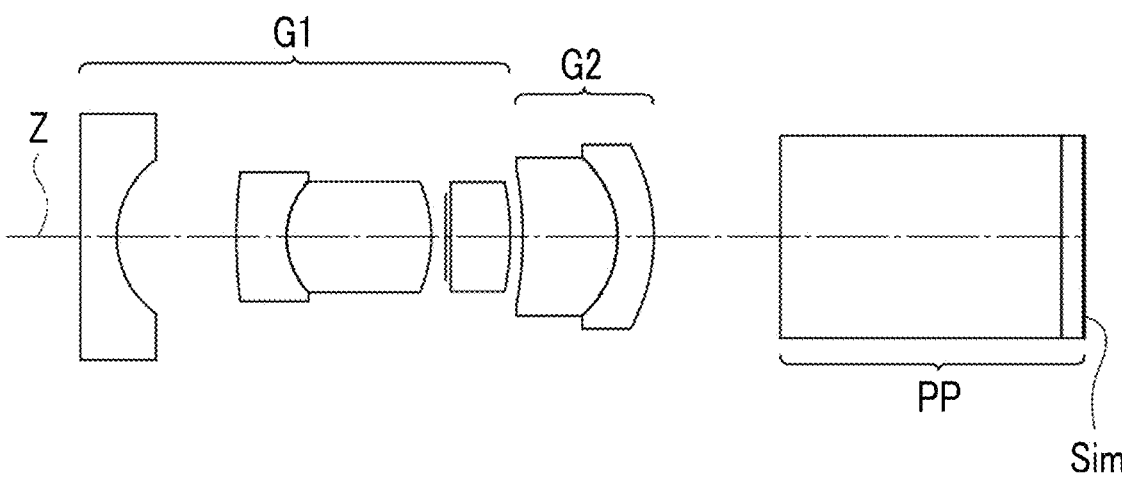

A cross-sectional view showing a configuration of an objective lens for an endoscope of example 5 is shown in FIG. 10. The objective lens for an endoscope of example 5 has the same configuration as the outline of the objective lens for an endoscope of example 1.

Each group of the objective lens for an endoscope of example 5 is composed as follows. The first a lens group G1a consists of the lens L11, the lens L12, and the lens L13 in order from the object side to the image side. The first b lens group G1b consists of the lens L14. The second lens group G2 consists of the lens L21 and the lens L22, in order from the object side to the image side. The lens L12 and the lens L13 are cemented to each other. The lens L21 and the lens L22 are cemented to each other. Each of the lens L11 and the lens L14 is a single lens.

Figure 11:
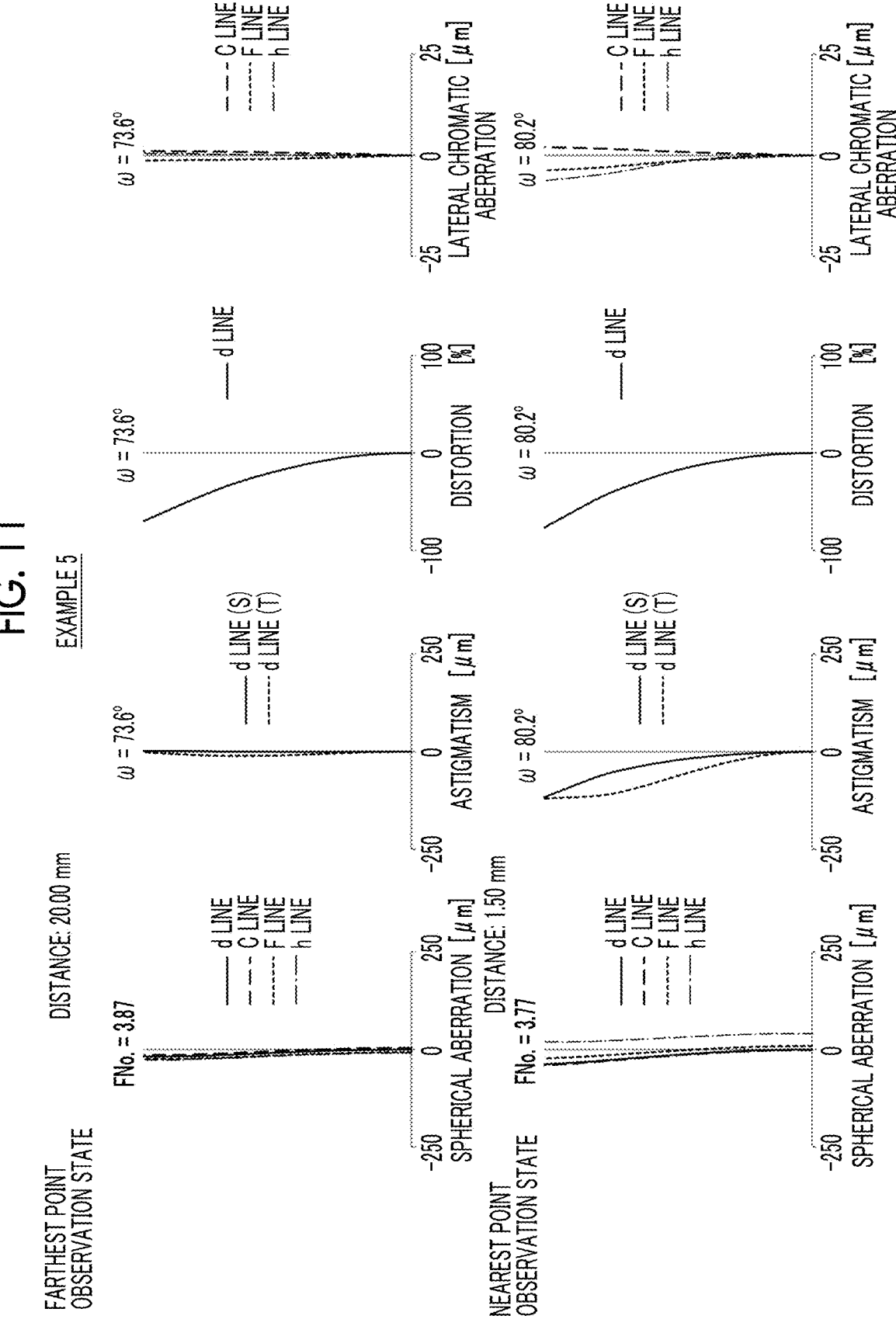
FIG. 11 is each aberration diagram of the objective lens for an endoscope of example 5.

Basic lens data of the objective lens for an endoscope of example 5 is shown in table 9, specifications and variable surface spacing thereof are shown in table 10, and each aberration diagram thereof is shown in FIG. 11.

TABLE 9

| | | Example 5 | | |
|---|---|---|---|---|
| Sn | R | D | Nd | νd |
| 1 | ∞ | 0.2500 | 1.88299 | 40.78 |
| 2 | 0.6649 | 0.8236 | | |
| 3 | 3.7510 | 0.3500 | 1.79472 | 48.53 |
| 4 | 0.5704 | 0.9967 | 1.57981 | 40.04 |
| 5 | −0.9501 | 0.1000 | | |
| 6(St) | ∞ | 0.0350 | | |
| 7 | ∞ | 0.4074 | 1.47510 | 83.83 |
| 8 | −1.8556 | DD[8] | | |
| 9 | −2.5640 | 0.6457 | 1.72425 | 55.29 |
| 10 | −0.7402 | 0.2500 | 1.94595 | 17.98 |
| 11 | −1.3417 | DD[11] | | |

TABLE 9-continued

| | | Example 5 | | |
|---|---|---|---|---|
| Sn | R | D | Nd | νd |
| 12 | ∞ | 1.9400 | 1.55919 | 53.90 |
| 13 | ∞ | 0.1500 | 1.51633 | 64.06 |
| 14 | ∞ | 0.0100 | | |

TABLE 10

| | Example 5 | |
|---|---|---|
| | Farthest point | Nearest point |
| Focal length | 0.696 | 0.646 |
| Back focus | 1.762 | 2.018 |
| F-number | 3.87 | 3.77 |
| Maximum total angle of view [°] | 147.3 | 160.4 |
| Maximum image height | 0.700 | 0.700 |
| Object distance | 20.00 | 1.50 |
| Paraxial imaging magnification | −0.0338 | −0.3163 |
| DD[8] | 0.5221 | 0.0857 |
| DD[11] | 0.4326 | 0.8690 |

Table 11 shows corresponding values of conditional expressions (1) to (14) of the objective lenses for an endoscope of examples 1 to 5. Table 11 shows values based on the d line. Preferable ranges of the conditional expressions may be set using the corresponding values of the examples shown in table 11 as upper limit values or lower limit values of the conditional expressions.

TABLE 11

| Expression number | Expression | Example 1 | Example 2 | Example 3 | Example 4 | Example 5 |
|---|---|---|---|---|---|---|
| (1) | $Y/(fF \times \tan\omega f)$ | 0.376 | 0.252 | 0.374 | 0.217 | 0.296 |
| (2) | $f1/f2$ | 0.160 | 0.156 | 0.193 | 0.211 | 0.194 |
| (3) | $fL1/fF$ | −0.876 | −0.950 | −0.812 | −0.842 | −1.083 |
| (4) | $FNof/\tan\omega f$ | 1.551 | 0.939 | 1.176 | 0.639 | 1.138 |
| (5) | $fF/f1$ | 0.801 | 0.815 | 0.835 | 0.787 | 0.794 |
| (6) | $fF/f2$ | 0.128 | 0.127 | 0.161 | 0.166 | 0.154 |
| (7) | $fL1/f1$ | −0.702 | −0.774 | −0.677 | −0.662 | −0.860 |
| (8) | $fF/f1a$ | 0.181 | 0.008 | 0.544 | 0.099 | 0.218 |
| (9) | $f1/f1a$ | 0.227 | 0.010 | 0.652 | 0.126 | 0.275 |
| (10) | $fF/f1b$ | 0.204 | 0.258 | 0.118 | 0.213 | 0.178 |
| (11) | $f1/f1b$ | 0.254 | 0.317 | 0.142 | 0.271 | 0.224 |
| (12) | $(fF/|M|) \times (\beta f/\beta n)$ | 0.277 | 0.272 | 0.259 | 0.478 | 0.171 |
| (13) | $|\nu 1p - \nu 1n|$ | 36.66 | 30.11 | 36.66 | 5.63 | 8.49 |
| (14) | $|\nu 2p - \nu 2n|$ | 69.20 | 26.97 | 30.07 | 56.72 | 37.31 |

The objective lenses for an endoscope of examples 1 to 5 have a total angle of view of 135° or more in the farthest observation state while being configured to be small in size, and thus a wide angle of view is secured. In addition, the objective lenses for an endoscope of examples 1 to 5 do not have a large change in performance between the farthest point observation state and the nearest point observation state and maintain high optical performances since the aberrations thereof are favorably corrected in both states.

Figure 12:
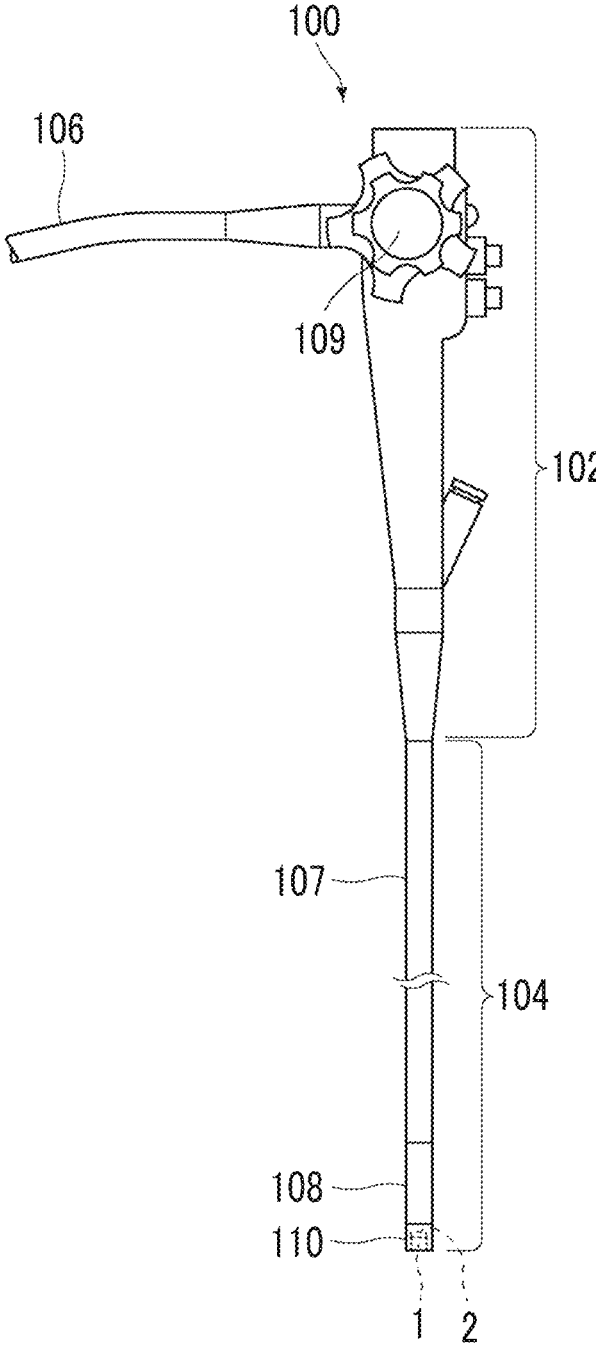
FIG. 12 is a schematic configuration view of the endoscope according to the embodiment.

Next, an endoscope according to the embodiment of the disclosure will be described. FIG. 12 is a schematic overall configuration view of the endoscope according to the embodiment of the present disclosure. An endoscope 100 shown in FIG. 12 mainly comprises an operating part 102, an insertion part 104, and a universal cord 106 that is to be connected to a connector portion (not shown). A large portion of the insertion part 104 is a soft portion 107 that bends in any direction along an insertion path, a bendable part 108 is connected to a distal end of the soft portion 107, and a distal end portion 110 is connected to a distal end of the bendable part 108. The bendable part 108 is provided to allow the distal end portion 110 to face a desired direction and can be operated to be bent by the rotational movement of a bending operation knob 109 provided at the operating part 102. An objective lens for an endoscope 1 according to the embodiment of the present disclosure and an imaging element 2 are provided at an inner distal end of the distal end portion 110. The imaging element 2 is, for example, a charge coupled device (CCD), a complementary metal oxide semiconductor (CMOS), or the like. The imaging element 2 is disposed so that an imaging area thereof coincides with an image plane of the objective lens for an endoscope 1. FIG. 12 is a conceptual view showing the objective lens for an endoscope 1 and the imaging element 2.

The technique of the present disclosure has been hitherto described through the embodiment and the examples, but the technique of the present disclosure is not limited to the embodiment and the examples, and various modifications are possible. For example, a curvature radius, surface spacing, a refractive index, an Abbe number, and the like of each lens may have other values without being limited to values shown in each numerical example.

The following supplementary notes are further disclosed with respect to the embodiment and the examples described above.

Supplementary Note 1

An objective lens for an endoscope consisting of, in order from an object side to an image side, a first lens group having positive optical power; and a second lens group having positive optical power, in which during focusing from a farthest point object to a nearest point object, the first lens group is fixed to an image plane, and only the second lens group moves along an optical axis, the first lens group includes a single lens having negative optical power closest to the object side, and in a case where a maximum image height is denoted by Y, a focal length of a whole system in a state where the farthest point object is in focus is denoted by $fF$, a maximum half angle of view in the state where the farthest point object is in focus is denoted by $\omega f$, a focal length of the first lens group is denoted by $f1$, a focal length of the second lens group is denoted by $f2$, and a focal length of the single lens is denoted by $fL1$, conditional expressions (1), (2), and (3) are satisfied, which are represented by $$0 < Y/(fF \times \tan \omega f) < 0.6 \tag{1,}$$

$$0 < f1/f2 < 0.25 \tag{2, and}$$

$$-1.2 < fL1/fF < 0 \tag{3.}$$

Supplementary Note 2

The objective lens for an endoscope according to supplementary note 1, in which in a case where an F-number in the state where the farthest point object is in focus is denoted by FNof, conditional expression (4) is satisfied, which is represented by $$0 < FNof/\tan \omega f < 2 \tag{4.}$$

Supplementary Note 3

The objective lens for an endoscope according to supplementary note 1 or 2, in which expression (5) is satisfied, which is represented by $$0 < fF/f1 < 2 \tag{5.}$$

Supplementary Note 4

The objective lens for an endoscope according to any one of supplementary notes 1 to 3, in which conditional expression (6) is satisfied, which is represented by $$0 < fF/f2 < 0.5 \tag{6.}$$

Supplementary Note 5

The objective lens for an endoscope according to any one of supplementary notes 1 to 4, in which conditional expression (7) is satisfied, which is represented by $$-1.5 < fL1/f1 < 0 \tag{7.}$$

Supplementary Note 6

The objective lens for an endoscope according to any one of supplementary notes 1 to 5, in which a lens surface of the single lens on the object side is a plane.

Supplementary Note 7

The objective lens for an endoscope according to any one of supplementary notes 1 to 6, in which the first lens group consists of, in order from the object side to the image side, a first a lens group having positive optical power, an aperture stop, and a first b lens group having positive optical power, and in a case where a focal length of the first a lens group is denoted by $f1a$, conditional expression (8) is satisfied, which is represented by $$0 < fF/f1a < 1 \tag{8.}$$

Supplementary Note 8

The objective lens for an endoscope according to any one of supplementary notes 1 to 7, in which the first lens group consists of, in order from the object side to the image side, a first a lens group having positive optical power, an aperture stop, and a first b lens group having positive optical power, and in a case where a focal length of the first a lens group is denoted by $f1a$, conditional expression (9) is satisfied, which is represented by $$0 < f1/f1a < 1 \tag{9.}$$

Supplementary Note 9

The objective lens for an endoscope according to any one of supplementary notes 1 to 8, in which the first lens group consists of, in order from the object side to the image side, a first a lens group having positive optical power, an aperture stop, and a first b lens group having positive optical power, and in a case where a focal length of the first b lens group is denoted by $f1b$, conditional expression (10) is satisfied, which is represented by $$0 < fF/f1b < 1 \tag{10.}$$

Supplementary Note 10

The objective lens for an endoscope according to any one of supplementary notes 1 to 9, in which the first lens group consists of, in order from the object side to the image side, a first a lens group having positive optical power, an aperture stop, and a first b lens group having positive optical power, and in a case where a focal length of the first b lens group is denoted by f1b, conditional expression (11) is satisfied, which is represented by $$0 < f1/f1b < 1 \tag{11}.$$

Supplementary Note 11

The objective lens for an endoscope according to any one of supplementary notes 1 to 10, in which in a case where, during focusing from the farthest point object to the nearest point object, a distance by which the second lens group moves is denoted by M, a paraxial imaging magnification of the whole system in the state where the farthest point object is in focus is denoted by $\beta f$, and a paraxial imaging magnification of the whole system in a state where the nearest point object is in focus is denoted by $\beta n$, conditional expression (12) is satisfied, which is represented by $$0.01 < (fF/|M|) \times (\beta f/\beta n) < 1 \tag{12}.$$

Supplementary Note 12

The objective lens for an endoscope according to any one of supplementary notes 1 to 11, in which the first lens group consists of, in order from the object side to the image side, a first a lens group having positive optical power, an aperture stop, and a first b lens group having positive optical power, and the first a lens group includes a cemented lens in which at least one negative lens and at least one positive lens are cemented.

Supplementary Note 13

The objective lens for an endoscope according to supplementary note 12, in which in a case where an average value of abbe numbers of all the positive lenses included in the cemented lens of the first a lens group based on a d line is denoted by v1p, and an average value of abbe numbers of all the negative lenses included in the cemented lens of the first a lens group based on the d line is denoted by v1n, conditional expression (13) is satisfied, which is represented by $$0 < |v1p - v1n| < 40 \tag{13}.$$

Supplementary Note 14

The objective lens for an endoscope according to any one of supplementary notes 1 to 13, in which the second lens group includes a cemented lens in which at least one negative lens and at least one positive lens are cemented.

Supplementary Note 15

The objective lens for an endoscope according to any one of supplementary notes 1 to 14, in which the second lens group consists of one cemented lens in which at least one negative lens and at least one positive lens are cemented.

Supplementary Note 16

The objective lens for an endoscope according to supplementary note 14, in which in a case where an average value of abbe numbers of all the positive lenses included in the cemented lens of the second lens group based on a d line is denoted by v2p, and an average value of abbe numbers of all the negative lenses included in the cemented lens of the second lens group based on the d line is denoted by v2n, conditional expression (14) is satisfied, which is represented by $$25 < |v2p - v2n| < 85 \tag{14}.$$

Supplementary Note 17

An endoscope comprising the objective lens for an endoscope according to any one of supplementary notes 1 to 16.

What is claimed is:

1. An objective lens for an endoscope consisting of, in order from an object side to an image side, a first lens group having positive optical power; and a second lens group having positive optical power, wherein during focusing from a farthest point object to a nearest point object, the first lens group is fixed to an image plane, and only the second lens group moves along an optical axis, the first lens group includes a single lens having negative optical power closest to the object side, and in a case where a maximum image height is denoted by Y, a focal length of the objective lens for an endoscope in a state where the farthest point object is in focus is denoted by fF, a maximum half angle of view in the state where the farthest point object is in focus is denoted by ωf, a focal length of the first lens group is denoted by f1, a focal length of the second lens group is denoted by f2, and a focal length of the single lens is denoted by fL1, conditional expressions (1), (2), and (3) are satisfied, which are represented by $$0 < Y/(fF \times \tan \omega f) < 0.6 \tag{1},$$

$$0 < f1/f2 < 0.25 \tag{2, and}$$

$$-1.2 < fL1/fF < 0 \tag{3}.$$

2. The objective lens for an endoscope according to claim 1, wherein in a case where an F-number in the state where the farthest point object is in focus is denoted by FNof, conditional expression (4) is satisfied, which is represented by $$0 < FNof/\tan \omega f < 2 \tag{4}.$$

3. The objective lens for an endoscope according to claim 1, wherein conditional expression (5) is satisfied, which is represented by $$0 < fF/f1 < 2 \tag{5}.$$

4. The objective lens for an endoscope according to claim 1, wherein conditional expression (6) is satisfied, which is represented by $$0 < fF/f2 < 0.5 \tag{6}.$$

5. The objective lens for an endoscope according to claim 1, wherein conditional expression (7) is satisfied, which is represented by $$-1.5<fL1/f1<0 \tag{7}.$$

6. The objective lens for an endoscope according to claim 1, wherein a lens surface of the single lens on the object side is a plane.

7. The objective lens for an endoscope according to claim 1, wherein the first lens group consists of, in order from the object side to the image side, a first a lens group having positive optical power, an aperture stop, and a first b lens group having positive optical power, and in a case where a focal length of the first a lens group is denoted by f1a, conditional expression (8) is satisfied, which is represented by $$0<fF/f1a<1 \tag{8}.$$

8. The objective lens for an endoscope according to claim 1, wherein the first lens group consists of, in order from the object side to the image side, a first a lens group having positive optical power, an aperture stop, and a first b lens group having positive optical power, and in a case where a focal length of the first a lens group is denoted by f1a, conditional expression (9) is satisfied, which is represented by $$0<f1/f1a<1 \tag{9}.$$

9. The objective lens for an endoscope according to claim 1, wherein the first lens group consists of, in order from the object side to the image side, a first a lens group having positive optical power, an aperture stop, and a first b lens group having positive optical power, and in a case where a focal length of the first b lens group is denoted by f1b, conditional expression (10) is satisfied, which is represented by $$0<fF/f1b<1 \tag{10}.$$

10. The objective lens for an endoscope according to claim 1, wherein the first lens group consists of, in order from the object side to the image side, a first a lens group having positive optical power, an aperture stop, and a first b lens group having positive optical power, and in a case where a focal length of the first b lens group is denoted by f1b, conditional expression (11) is satisfied, which is represented by $$0<f1/f1b<1 \tag{11}.$$

11. The objective lens for an endoscope according to claim 1, wherein in a case where, during focusing from the farthest point object to the nearest point object, a distance by which the second lens group moves is denoted by M, a paraxial imaging magnification of the objective lens for an endoscope in the state where the farthest point object is in focus is denoted by βf, and a paraxial imaging magnification of the objective lens for an endoscope in a state where the nearest point object is in focus is denoted by βn, conditional expression (12) is satisfied, which is represented by $$0.01<(fF/|M|)\times(\beta f/\beta n)<1 \tag{12}.$$

12. The objective lens for an endoscope according to claim 1, wherein the first lens group consists of, in order from the object side to the image side, a first a lens group having positive optical power, an aperture stop, and a first b lens group having positive optical power, and the first a lens group includes a cemented lens in which at least one negative lens and at least one positive lens are cemented.

13. The objective lens for an endoscope according to claim 12, wherein in a case where an average value of abbe numbers of all the positive lenses included in the cemented lens of the first a lens group based on a d line is denoted by v1p, and an average value of abbe numbers of all the negative lenses included in the cemented lens of the first a lens group based on the d line is denoted by v1n, conditional expression (13) is satisfied, which is represented by $$0<|v1p-v1n|<40 \tag{13}.$$

14. The objective lens for an endoscope according to claim 1, wherein the second lens group includes a cemented lens in which at least one negative lens and at least one positive lens are cemented.

15. The objective lens for an endoscope according to claim 1, wherein the second lens group consists of one cemented lens in which at least one negative lens and at least one positive lens are cemented.

16. The objective lens for an endoscope according to claim 14, wherein in a case where an average value of abbe numbers of all the positive lenses included in the cemented lens of the second lens group based on a d line is denoted by v2p, and an average value of abbe numbers of all the negative lenses included in the cemented lens of the second lens group based on the d line is denoted by v2n, conditional expression (14) is satisfied, which is represented by $$25<|v2p-v2n|<85 \tag{14}.$$

17. An endoscope comprising the objective lens for an endoscope according to claim 1.

* * * * *